US010959762B2

(12) United States Patent
Williams

(10) Patent No.: US 10,959,762 B2
(45) Date of Patent: *Mar. 30, 2021

(54) INTRAMEDULLARY ROD PLATE SYSTEM

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 19 days.

This patent is subject to a terminal disclaimer.

(21) Appl. No.: 16/238,684

(22) Filed: Jan. 3, 2019

(65) Prior Publication Data

US 2019/0133651 A1 May 9, 2019

Related U.S. Application Data

(63) Continuation of application No. 15/581,508, filed on Apr. 28, 2017, now Pat. No. 10,206,724.

(51) Int. Cl.
*A61B 17/72* (2006.01)
*A61B 17/80* (2006.01)
*A61B 17/86* (2006.01)

(52) U.S. Cl.
CPC ........ *A61B 17/7241* (2013.01); *A61B 17/725* (2013.01); *A61B 17/809* (2013.01); *A61B 17/8695* (2013.01)

(58) Field of Classification Search
CPC . A61B 17/7241; A61B 17/725; A61B 17/809; A61B 17/8695; A61B 17/8033; A61B 17/72; A61B 17/746; A61B 17/80; A61B 17/8605; A61B 17/8625; A61B 17/8061; A61B 17/744; A61B 17/921; A61B 17/1725; A61B 17/7225; A61B 17/7233; A61B 17/1775; A61B 2017/0004

USPC .......... 606/62–68, 86 R, 324, 281, 297, 232
See application file for complete search history.

(56) References Cited

U.S. PATENT DOCUMENTS

| | | | | |
|---|---|---|---|---|
| 8,486,072 B2 * | 7/2013 | Haininger | ......... | A61B 17/8061 606/64 |
| 9,066,764 B2 * | 6/2015 | Perez | ................. | A61B 17/7233 |
| 9,861,492 B2 * | 1/2018 | Ek | ......................... | A61F 2/4637 |
| 10,206,724 B2 * | 2/2019 | Williams | ........... | A61B 17/7241 |
| 10,314,626 B2 * | 6/2019 | Koay | ................. | A61B 17/7241 |
| 2009/0306664 A1 * | 12/2009 | Teeny | .................. | A61B 17/725 606/64 |
| 2010/0256685 A1 * | 10/2010 | Plecko | ............... | A61B 17/8061 606/281 |
| 2018/0125506 A1 * | 5/2018 | Song | .................. | A61B 17/1666 |

* cited by examiner

*Primary Examiner* — Pedro Philogene
(74) *Attorney, Agent, or Firm* — Bell & Manning, LLC; Christopher Kalafut

(57) ABSTRACT

A system to stabilize a fracture includes an intramedullary rod having first and second ends and configured for placement within a medullary bone canal of a bone. The intramedullary rod includes a first rod hole at the second end. An intramedullary rod plate has first and second plate holes. A first fastener includes a shaft portion and a threaded head portion. The shaft portion of the first fastener passes through the first plate hole, through an outer surface of the bone, and through the first rod hole at the second end of the intramedullary rod such that the first fastener secures the intramedullary rod plate to the intramedullary rod. The threaded head portion of the first fastener mates with threads in the first plate hole. A second fastener passes through the second plate hole and into the bone to secure the intramedullary rod plate to the bone.

18 Claims, 15 Drawing Sheets

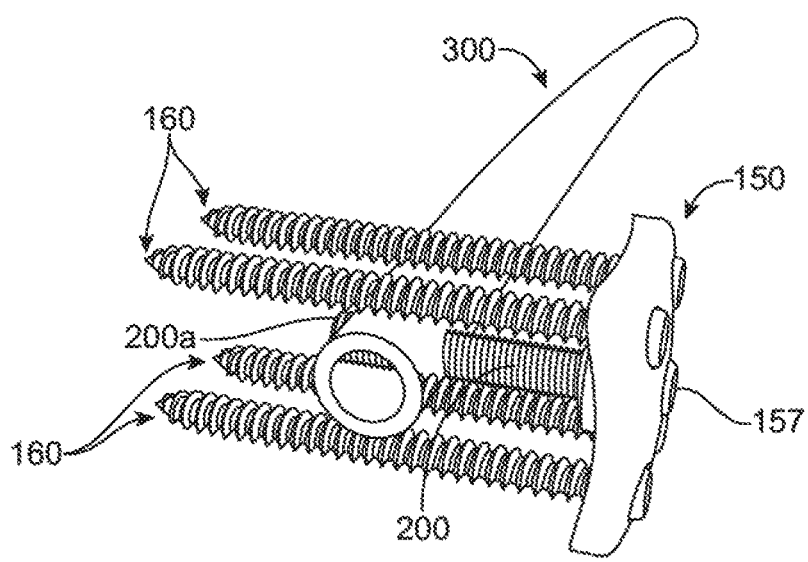
FIG. 9A
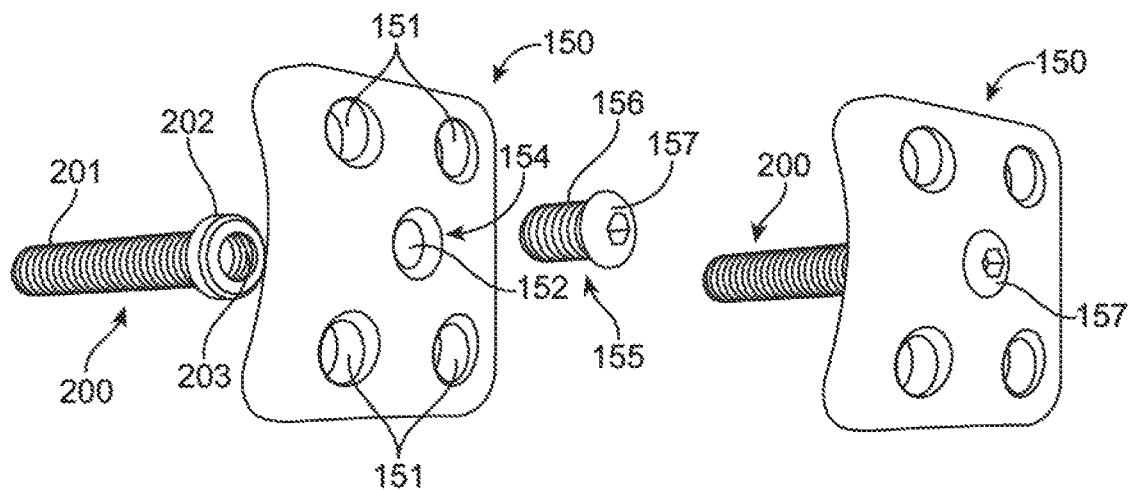
FIG. 9B
FIG. 9C
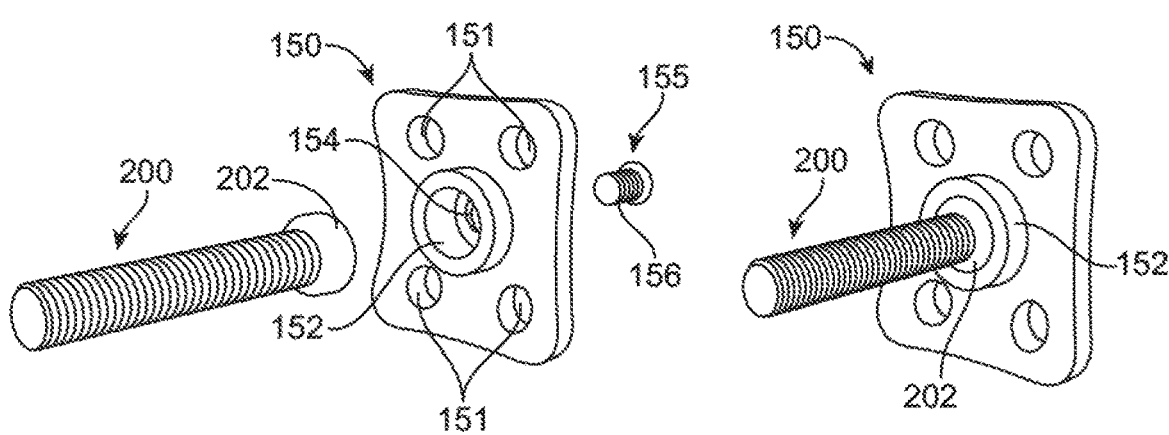
FIG. 9D
FIG. 9E

INTRAMEDULLARY ROD PLATE SYSTEM

CROSS-REFERENCE TO RELATED APPLICATION

The present application claims priority as a continuation application of U.S. patent application Ser. No. 15/581,508 filed on Apr. 28, 2017, the entire disclosure of which is incorporated herein by reference.

BACKGROUND

The following description is provided to assist the understanding of the reader. None of the information provided or references cited is admitted to be prior art.

Fractures or other conditions that cause instability of a long bone may be stabilized with intramedullary rod fixation, or otherwise known as intramedullary nail fixation. In this type of fixation procedure, an implant such as an intramedullary rod or nail is inserted through either the proximal or distal end of a long bone into the medullary canal. The rod diameter is chosen to be slightly smaller than the diameter of the medullary canal, such that the rod can be passed along the length of the long bone, while still providing a frictional interference fit between the outer surface of the rod and the surface of the medullary canal. The rod is passed across the fracture (or other area of bony instability, but for purposes of brevity, will henceforth be referenced as a fracture), and due to the rod frictional interference fit of the rod with the medullary canal of the bone both proximal and distal to the fracture, some degree of stability is restored.

SUMMARY

An illustrative system to stabilize a fracture includes an intramedullary rod having a first end and a second end and configured for placement within a medullary bone canal of a bone. The intramedullary rod includes a first rod hole at the second end. The system also includes an intramedullary rod plate having a first plate hole and a second plate hole. The system also includes a first fastener configured to be received by the first plate hole, wherein the first fastener passes through an outer surface of the bone and through the first rod hole at the second end of the intramedullary rod such that the first fastener secures the intramedullary rod plate to the intramedullary rod. The system further includes a second fastener configured to pass through the second plate hole and into the bone such that the second listener secures the intramedullary rod plate to the bone.

An illustrative method to stabilize a fracture includes placing an intramedullary rod having a first end and a second end into a medullary bone canal of a bone, where the intramedullary rod includes a first rod hole at the second end. The method also includes placing an intramedullary rod plate proximate to the second end of the intramedullary rod, where the intramedullary rod plate includes a first plate hole and a second plate hole. The method also includes placing a first fastener in contact with the first plate hole, through an outer surface of the bone, and through the first rod hole at the second end of the intramedullary rod to secure the intramedullary rod plate to the intramedullary rod. The method further comprises placing a second fastener through the second plate hole and into the bone to secure the intramedullary rod plate to the bone.

Another illustrative system to stabilize a fracture includes an intramedullary rod having a first end and a second end and configured for placement within a medullary bone canal of a bone. The intramedullary rod includes a first rod hole at the second end. The system also includes an intramedullary rod plate having a first plate hole and a second plate hole. The system also includes a first fastener that includes a shaft portion and a threaded head portion. The shaft portion of the first fastener passes through the first plate hole, through an outer surface of the bone, and through the first rod hole at the second end of the intramedullary rod such that the first fastener secures the intramedullary rod plate to the intramedullary rod. The threaded head portion of the first fastener mates with threads in the first plate hole. The system further includes a second fastener configured to pass through the second plate hole and into the bone such that the second fastener secures the intramedullary rod plate to the bone.

Another illustrative method to stabilize a fracture includes placing an intramedullary rod having a fast end and a second end into a medullary bone canal of a bone, where the intramedullary rod includes a first rod hole at the second end. The method also includes placing an intramedullary rod plate proximate to the second end of the intramedullary rod, where the intramedullary rod plate includes a first plate hole and a second plate hole. The method also includes placing a first fastener such that a shaft portion of the first fastener passes through the first plate hole, through an outer surface of the bone, and through the first rod hole at the second end of the intramedullary rod to secure the intramedullary rod plate to the intramedullary rod and such that a threaded head portion of the first fastener mates with threads in the first plate hole. The method further includes placing a second fastener through the second plate hole and into the bone to secure the intramedullary rod plate to the bone.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 9A is a perspective view depicting the assembled intramedullary rod plate secured to the interlocking bolt that has been inserted into the intramedullary rod, with plate screws placed through the intramedullary rod plate, in accordance with an illustrative embodiment.

FIG. 9B is a perspective view depicting the interlocking bolt, intramedullary rod plate, and plate securing device in an assembly position, in accordance with an illustrative embodiment.

FIG. 9C is a perspective view depicting the assembled intramedullary rod plate secured to the interlocking bolt with the plate securing device, in accordance with an illustrative embodiment.

FIG. 9D is a perspective view depicting the interlocking bolt, intramedullary rod plate, and plate securing device in an assembly position, in accordance with illustrative embodiments.

FIG. 9E is a perspective view depicting the assembled intramedullary rod plate seated on the interlocking bolt, in accordance with an illustrative embodiment.

Figure 1A:
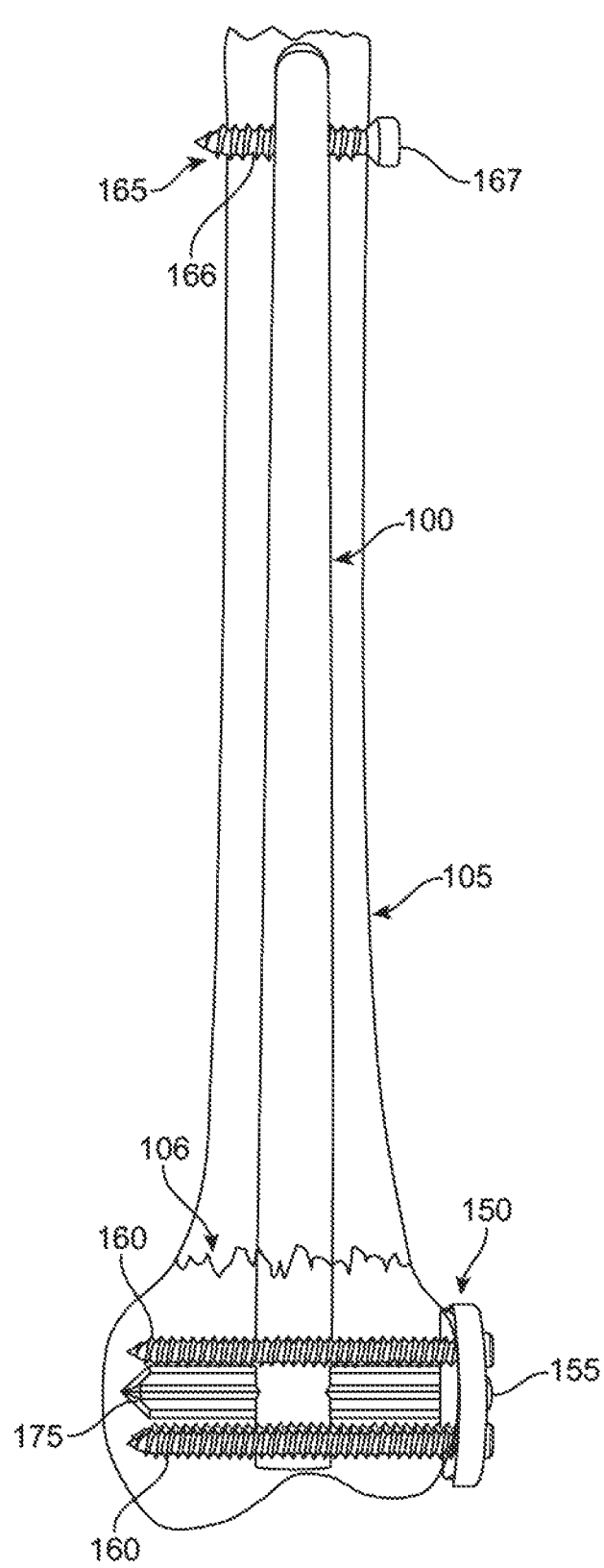
FIG. 1A is a top or anterior view depicting an intramedullary rod after insertion into a femur, with an interlocking blade fastener inserted through the distal end of the femur and through the rod, and the intramedullary rod plate being attached to the blade fastener, in accordance with an illustrative embodiment. The intramedullary rod plate is attached to the interlocking blade fastener, and plate screws have been inserted into the distal end of the femur through holes in the intramedullary rod plate, thus securing the intramedullary rod plate to the distal end of the femur.

The foregoing and other features of the present disclosure will become apparent from the following description and appended claims, taken, in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Intramedullary rod (alternatively called intramedullary nail) fixation of a long bone involves an intramedullary device and a method to insert the intramedullary device into the intramedullary canal of the long bone. The intramedullary rod is usually cylindrical but may have slots or grooves on the outer surface, depending on the design. In humans and animals, an intramedullary rod is commonly used to treat fractures (or other causes of instability such as tumors, infections, etc.) in a long bone, which in humans is most commonly the femur and tibia, but can also include the humerus, ulna, radius, and fibula. The intramedullary rod partially achieves stability by virtue of its frictional fit within the cancellous metaphyseal bone at one or both ends of the bone being treated, and within the medullary canal of the long bone proximal and distal to the fracture site. This stability can be augmented by passing interlocking screws, blades, or other fasteners from one bone surface through a reciprocal hole or holes in the intramedullary rod and out the opposite bone surface. These interlocking fasteners improve stability by further securing the intramedullary rod to the bone, but they depend on sufficient bone quantity and quality being present in the interlocking fastener zone, which typically is located at the terminal ends of the rod. In addition, the interlocking fasteners must pass through the intramedullary rod, further limiting the fixation options. This is typically not a problem when the fracture is located in the central diaphyseal bone region. However, when the fracture is located towards the proximal or distal end of the bone, the fixation options may be quite limited, in part because the surgeon must pass the interlocking fasteners through holes of the intramedullary rod that are located in a fixed position. The fixation options are particularly limiting in patients with compromised bone quality, such as in patients with osteopenia or osteoporosis.

Another scenario that poses problems with adequate interlocking fastener fixation is in patients who sustain periprosthetic fractures, especially in fractures that occur adjacent to a total knee arthroplasty, and in fractures near a joint (peri-articular) because the amount of bone present for interlocking fastener fixation may be minimal. Even when some bone is present in peri-articular fractures or fractures near a total knee prosthesis, the surgeon may not be able to achieve interlocking fastener fixation in this bone because the interlocking fastener trajectory is dictated by the location of the reciprocal interlocking fastener holes in the intramedullary rod. In these cases, interlocking fixation options can be limited or not possible, and intramedullary rod-assisted fixation of such fractures may be extremely difficult or not feasible. In such situations, even when an intramedullary rod-assisted fixation operation is performed, it may be prone to mechanical failure.

Depending on the fracture configuration, intramedullary rod fixation may not be appropriate or even possible, in which case, a plate is often used to fix the fracture because of the wider array of fixation options at the terminal end of the plate. When a plate is used, the incision(s) used to place the plate is/are usually substantially longer than the incision(s) used to place an intramedullary rod. The plate is placed on an outer surface of the fractured bone, and screws are placed through holes in the plate both proximal and distal to the fracture site in a configuration that secures the plate to the bone and in so doing achieves stability across the fracture site. One advantage to a plate when compared to an intramedullary rod is the wider array of fixation options at the terminal end of the plate, because the screws that are placed through the plate can be oriented in a variety of directions in order to achieve bony purchase, without the limitation of needing to pass through an intramedullary rod in order to achieve stability. One disadvantage of a plate when compared to an intramedullary rod is the greater degree of soft tissue disruption necessary to place the plate on the bone surface, which requires longer and more incisions, and disrupts muscle attachments thereby risking injury to neurovascular structures.

The present disclosure overcomes at least some of the disadvantages of existing intramedullary rod devices and methods, and existing plate devices and methods. Specifically, the surgical system of the present disclosure provides the advantages of intramedullary rod systems and the advantages of plate systems to maximize fixation options, while negating the disadvantages of these respective fracture fixation options. With the system of the present disclosure, bony fixation occurs on one side of the fracture with interlocking fasteners placed outside the intramedullary rod through an intramedullary rod plate that has a limited plate footprint compared to a conventional plate, with the fixation force achieved through the intramedullary rod plate transferred to the intramedullary rod at one end of the rod. Fixation on the other side of the fracture occurs with the intramedullary rod and interlocking fasteners in a conventional manner. The plate footprint is very much limited compared to a conventional plate fixation construct, because the disclosed intramedullary rod plate achieves fixation on only one side of the fracture, whereas a conventional plate must span the fracture site in order to achieve fixation on both sides of the fracture. The intramedullary rod plate system described herein allows for fixation on one side of the fracture with a plate and associated fasteners, and fixation on the other side of the fracture with the intramedullary rod and associated fasteners, thus maximizing the advantages and minimizing the disadvantages of conventional intramedullary rod and plate systems.

In particular, the intramedullary rod plate system of the present disclosure includes an intramedullary rod plate that attaches to an interlocking fastener that is connected to the intramedullary rod, and screws that pass through the intramedullary rod plate in order to achieve bony fixation outside the rod. Fixation is achieved on one side of the fracture primarily by virtue of the intramedullary rod's frictional fit within the medullary bone canal, whereas fixation is achieved on the other side of the fracture by virtue of the intramedullary rod plate (and associated screws) that is attached to the interlocking fastener that is in turn attached to the intramedullary rod. The intramedullary rod plate is much smaller than a conventional plate, because the plate itself need not cross the fracture site. Instead, the intramedullary rod plate is held in position by its attachment to the intramedullary rod, which then allows the surgeon to pass screws in a variety of trajectories through holes in the intramedullary rod plate and into available bone in order to achieve fixation. Placement of the intramedullary rod plate requires smaller and fewer incisions and less soft tissue disruption than placing a conventional plate.

By virtue of using the surgical system of the present disclosure, the intramedullary rod plate system may be used to treat such conditions such as, for example, peri-articular, peri-prosthetic, metaphyseal, and diaphyseal fractures of the femur, tibia, humerus, fibula, radius, clavicle, and ulna. The intramedullary rod plate system may also be used to achieve stability in the aforementioned long bones due to conditions such as tumor and infection. The intramedullary rod plate system may be employed for surgical treatments in a patient in a lateral, supine, oblique, or prone position, and may employ various approaches to the bones being treated. The intramedullary rod plate system may be used, in addition to humans, on animals, bone models, and other non-viable substrates, for example, for use in testing, demonstration, and training Referring now to FIG. 1A, a top or anterior view depicting an intramedullary rod plate system in an assembled position after retrograde insertion of an intramedullary rod 100 into the intramedullary canal of a femur 105 in order to stabilize distal femur metaphyseal fracture 106 is shown, in accordance with an illustrative embodiment. A human femur bone is used as an example henceforth, but should not be considered limiting with respect to application of the intramedullary rod plate system to other bones and other non-viable substrates. For example, the systems described herein can be used on other types of bone fractures such as tibia fractures, humerus fractures, etc. in humans or animals. Additionally, several of the embodiments herein are described with reference to a distal fracture. However, it should be understood that the systems of the present application can also be used on proximal fractures. The intramedullary rod plate system includes an intramedullary rod plate 150, plate bone screw fasteners 160, and a plate securing device 155 (partially shown) that secures the intramedullary rod plate 150 to an interlocking blade fastener 175 (henceforth referred to as an interlocking blade 175). In some embodiments, four plate bone screw fasteners 160 (henceforth referred to as plate screw(s) 160) are used. It is noted that only two plate screws are fully visible in FIG. 1A because in this top view the two plate screws closest to the viewer overlap the two plate screws most distant from the viewer. In alternative embodiments, additional or fewer plate screws may be used. The plate screws 160 are inserted through the intramedullary rod plate 150 and into femoral bone distal to fracture 106. Fracture fixation distal to the fracture occurs by transferring the bone fixation force achieved with screws 160 (that are inserted into distal femur bone) to the intramedullary rod plate 150, which in turn transfers this force to intramedullary rod 100 through the attachment of interlocking blade 175 to both the intramedullary rod plate 150 and the intramedullary rod 100. Interlocking blade 175 also may have an interference fit with distal femur bone, further conferring fixation distal to fracture 106.

Conventional intramedullary rod fixation of this type of distal femur fracture, as well as peri-articular and peri-prosthetic fractures, depends primarily on an interlocking blade or other fixation implement such as a screw to achieve fixation within distal femur bone on one or both sides of an intramedullary rod. In such conventional systems, interlocking fastener fixation is achieved with a fictional fit of the interlocking blade or interlocking screw(s) with distal femur bone on one or preferably both sides of the intramedullary rod. The interlocking fastener fixation force is transferred to the rod by virtue of the interlocking fastener either fitting with minimal tolerance through the hole in the intramedullary rod, or by virtue of a locking screw or fastener that is passed through the opening in the center of the cannulated intramedullary rod and engaged with the interlocking fastener. Therefore, the amount of fixation force achievable with a conventional intramedullary rod system is limited by the necessary passing of the interlocking fastener through a hole in the intramedullary rod. Even when multiple interlocking fasteners are used, they all must pass through holes in the intramedullary rod in order to provide stability.

The intramedullary rod plate system described herein allows for fixation outside the intramedullary rod, thus greatly expanding the fixation options because the surgeon no longer is limited by a requirement to pass all interlocking fasteners through the intramedullary rod. Instead, one interlocking fastener (or in alternative embodiments, two or more fasteners) is passed through the rod, with the primary purpose of providing a connection from the intramedullary rod to the intramedullary rod plate. The surgeon can then pass screws or other fasteners through holes in the intramedullary rod plate using a variety of trajectories aimed at available bone for fixation. Whereas in some embodiments the interlocking fastener that is passed through the intramedullary rod may also provide some stability via a frictional fit with surrounding bone as with a conventional intramedullary rod system, the primary purpose of the interlocking fastener used in the intramedullary rod plate system is to create a connection between the intramedullary rod located inside the bone and the intramedullary rod plate located on a surface of the bone.

Referring again to FIG. 1A, intramedullary rod fixation proximal to the fracture occurs via the frictional fit of the outer surface of the intramedullary rod 100 to the surface of the medullary canal of femur 105, and this proximal fixation may be augmented by placing one or more interlocking screws 165 (in some embodiments, comprised of threaded shaft portion 166 and head portion 167) or other fasteners through bone located towards the proximal end of the femur and through a hole or holes in the intramedullary rod 100 at the end of the intramedullary rod opposite the end of the rod with interlocking blade 175, in a manner known to those schooled in the art.

Figure 1B:
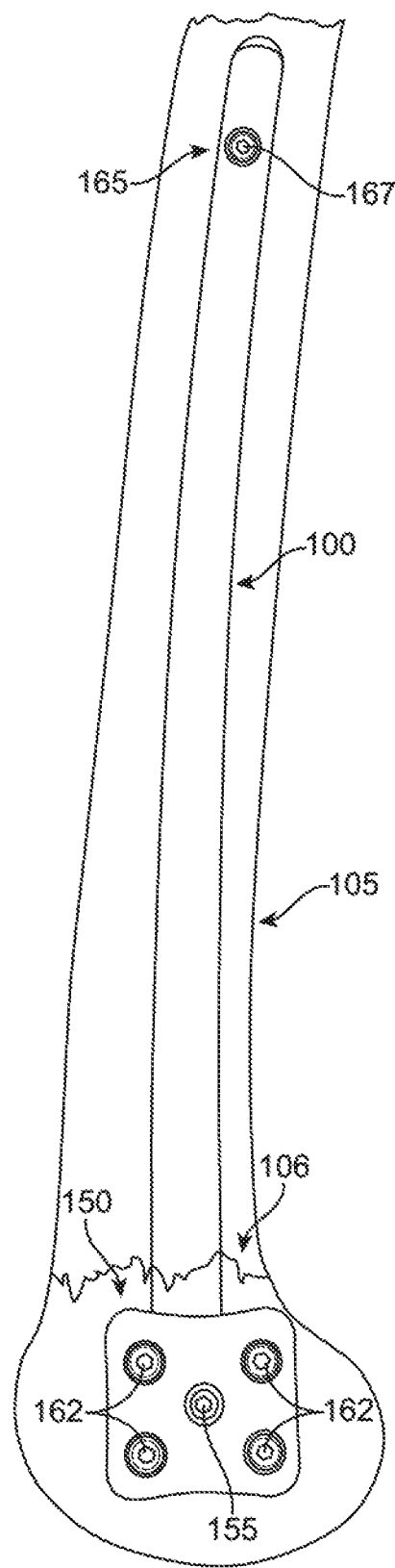
FIG. 1B is a side or lateral view depicting an intramedullary rod after insertion into a femur, with an interlocking blade fastener inserted through the distal end of the femur and through the rod, and the intramedullary rod plate being attached to the blade fastener, in accordance with an illustrative embodiment. The intramedullary rod plate is attached to the interlocking blade fastener, and plate screws have been inserted into the distal end of the femur through holes in the intramedullary rod plate, thus securing the intramedullary rod plate to the distal end of the femur.

Referring now to FIG. 1B in conjunction with FIG. 1A, a side or lateral view depicting an intramedullary rod plate system in an assembled position after retrograde insertion of an intramedullary rod 100 into the intramedullary canal of the femur 105 in order to stabilize distal femur fracture 106 is shown, in accordance with an illustrative embodiment. Retrograde insertion of the intramedullary rod insertion is performed through a hole drilled in the distal end of the femur, i.e., the knee, and the intramedullary rod is passed from the hole drilled in the distal end of the femur into the intramedullary canal and towards the hip, in a manner known to those schooled in the art. Intramedullary rod plate 150 is secured to the interlocking blade 175 by plate securing device 155, the head 157 of which is visible in FIG. 1B. It is noted that the interlocking blade 175 is not visible in FIG. 1B as it is covered by the intramedullary rod plate 150. In some embodiments, intramedullary rod plate 150 can include four holes to accommodate four plate screws 160 (not shown, plate screw heads 162 are shown here, representing plate screws 160 as seen in FIG. 1A). In alternative embodiments, intramedullary rod plate 150 can include more or fewer holes and can thus be used with more or fewer than four plate screws 160. In some embodiments, intramedullary rod plate 150 may be pre-contoured or contoured intra-operatively to closely match the local bony anatomy.

Intramedullary rod fixation proximal to the fracture occurs via the frictional fit of the outer surface of the intramedullary rod 100 to the surface of the medullary canal of femur 105, and this proximal fixation may be augmented by placing one or more interlocking screws 165 (as represented in this view by interlocking screw head 167) or fasteners through bone located towards the proximal end of the femur and through a hole or holes in the intramedullary rod 100 at the end of the intramedullary rod opposite the end of the rod with interlocking blade 175 (e.g., proximal interlocking screws), in a manner known to those schooled in the art.

The directions anterior-posterior, proximal-distal, and medial-lateral are well understood terms to people of skill in the art. For example, an anterior-posterior direction may refer to a horizontal, substantially horizontal, front-back, or back-front direction (e.g., the knee cap or patella is the anterior aspect of a human knee, and the skin crease on the back of the knee is the posterior aspect of a human knee), while a medial-lateral direction may refer to a horizontal, substantially horizontal, left-right, or right-left direction (e.g., left hand-right hand or right hand-left hand direction of a human body). Similarly, a proximal-distal direction or a superior-inferior direction may refer to a vertical, substantially vertical, top-bottom, or bottom-top direction (e.g., head-toe or toe-head direction of the human body, whereby the hip is the proximal part of the femur and the knee is the distal part of the femur).

Figure 2A:
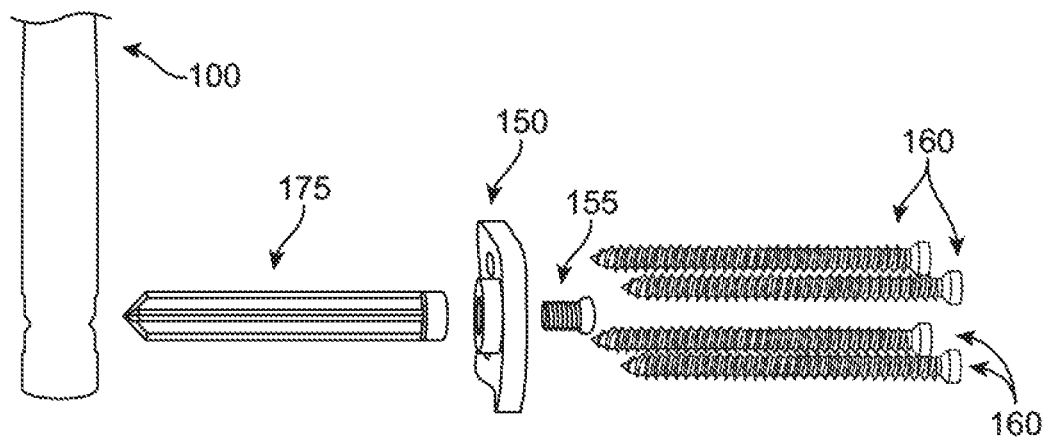
FIG. 2A is a top view depicting an intramedullary rod, interlocking blade, intramedullary rod plate, plate securing device, and plate screws in an assembling position, in accordance with illustrative embodiments.
Figure 2B:
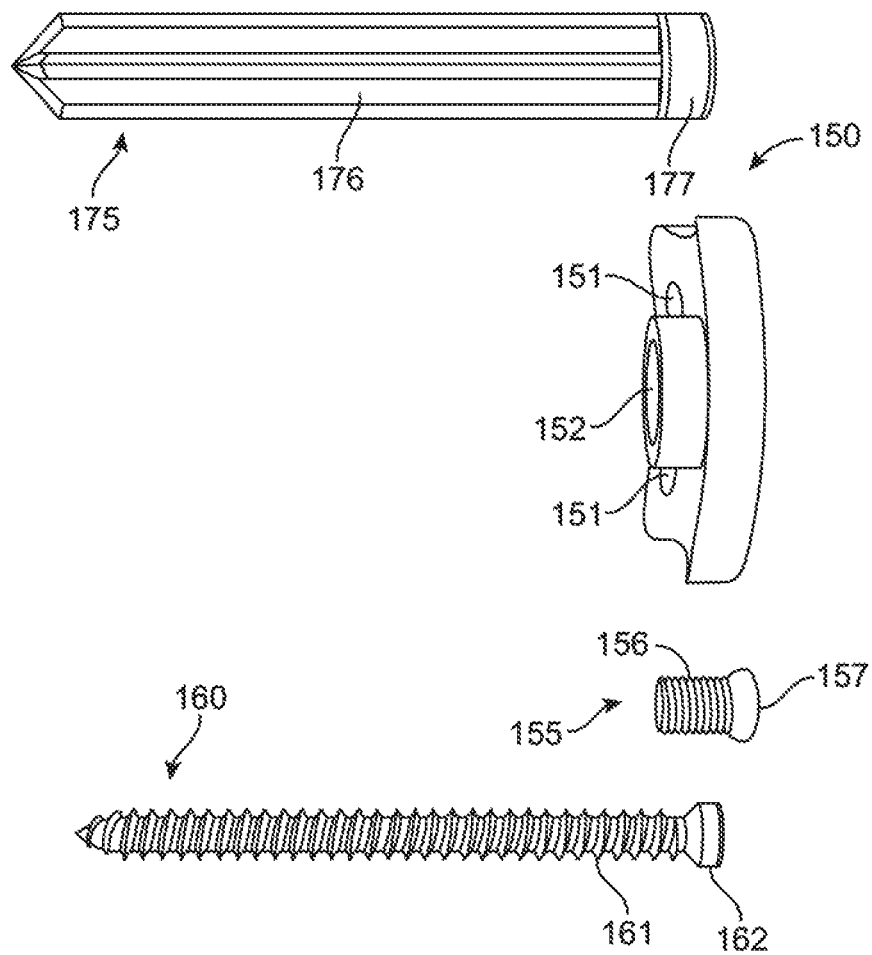
FIG. 2B is a close-up top view depicting an interlocking blade, intramedullary rod plate, plate securing device, and plate screws, in accordance with illustrative embodiments.

Referring now to FIG. 2A, a top view depicting an intramedullary rod 100, interlocking blade 175, intramedullary rod plate 150, plate securing device 155, and plate screws 160 in an assembling position are shown, in accordance with illustrative embodiments. FIG. 2B is a close-up top view depicting interlocking blade 175, intramedullary rod plate 150, plate securing device 155, and plate screws 160, in accordance with illustrative embodiments. In some embodiments, interlocking blade 175 includes a blade portion 176 that is designed to pass with minimal tolerance (thus providing some degree of frictional fit with the intramedullary rod) through a hole in the intramedullary rod and achieve bone fixation via a frictional interaction of the blade with surrounding bone. The interlocking blade 175 is attached to the intramedullary rod 100 via a fictional fit and/or via a bolt or other fastener that is configured to pass through one end of the rod and engage the interlocking blade 175. In some embodiments, interlocking blade 175 includes a blade head portion 177 that may be configured to attach to an insertion tool for use during insertion. The blade head portion 177 also serves the purpose of being a method of attachment to intramedullary rod plate 150 by fitting within a cylindrical receiving part 152 of the intramedullary rod plate 150. The attachment of intramedullary rod plate 150 to interlocking blade 175 is discussed in more detail with reference to FIGS. 4A-4C.

Figure 4A:
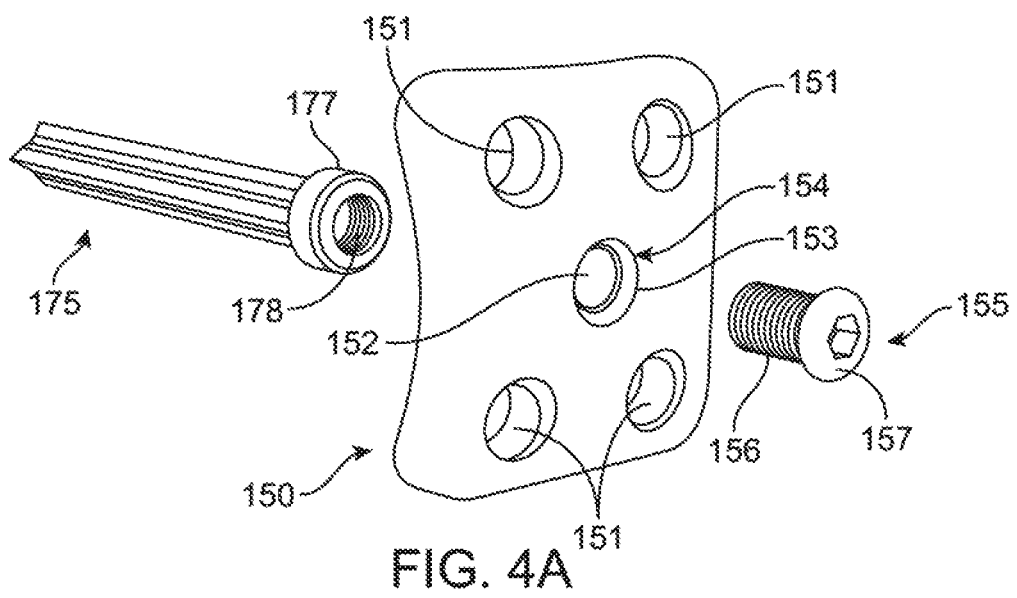
FIG. 4A is a perspective view depicting the interlocking blade, intramedullary rod plate, and plate securing device in an assembly position, in accordance with illustrative embodiments.
Figure 4B:
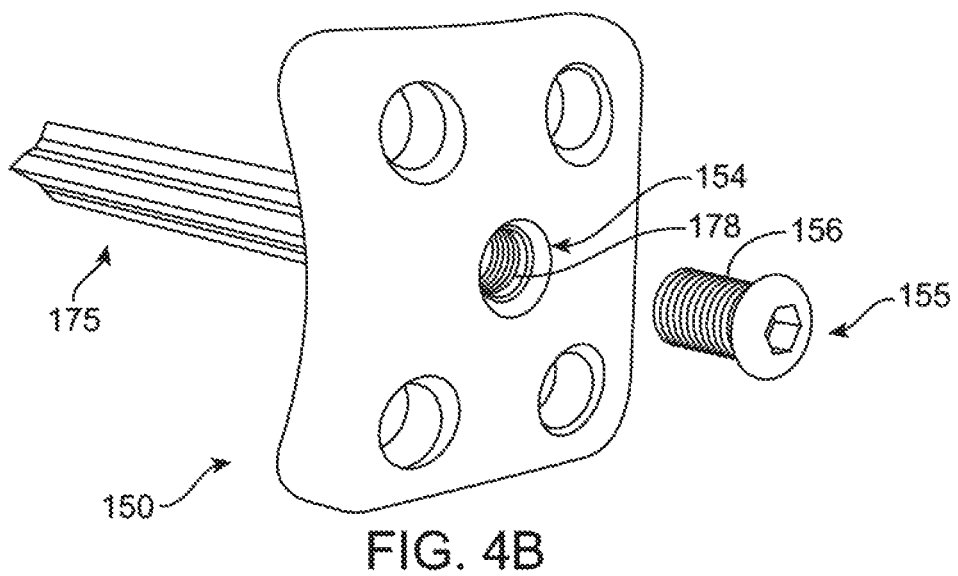
FIG. 4B is a perspective view depicting the intramedullary rod plate placed on the interlocking blade, with the plate securing device in an assembly position, in accordance with illustrative embodiments.

In some embodiments, plate fastener 155 includes a threaded shaft portion 156 that threads into a reciprocal threaded portion in blade head portion 177, as depicted in FIGS. 4A and 4B. Plate fastener 155 also includes a head portion 157. In some embodiments, intramedullary rod plate 150 includes two or more holes 151 to accommodate plate screws 160. In some embodiments, plate screws 160 include a threaded portion 161 that enables frictional fixation with bone, and a head portion 162 configured to attach to a screwdriver or other insertion device during screw insertion. In an illustrative embodiment, the head portion 162 serves the purpose of attaching to intramedullary rod plate 150 by pressing tightly into screw holes 151 during fracture fixation, creating a frictional fit. In some embodiments, the portion of plate screw head 162 that engages with intramedullary rod plate screw holes 151 may be configured with threads, with reciprocal threads configured in screw holes 151, in order to create a secure locked attachment between plate screws 160 and intramedullary rod plate 150 via the screw threads.

FIGS. 3A-3E depict the assembly sequence of an embodiment of the intramedullary rod plate system in accordance with an illustrative embodiment. Now turning to FIG. 3A, a top view depicting one end of intramedullary rod 100, with interlocking blade 175, intramedullary rod plate 150, plate securing device 155, and plate screws 160 are shown in an assembling position, in accordance with illustrative embodiments. Intramedullary rod 100 includes a hole 101 (partially shown) that accommodates interlocking blade 175.

Figure 3A:
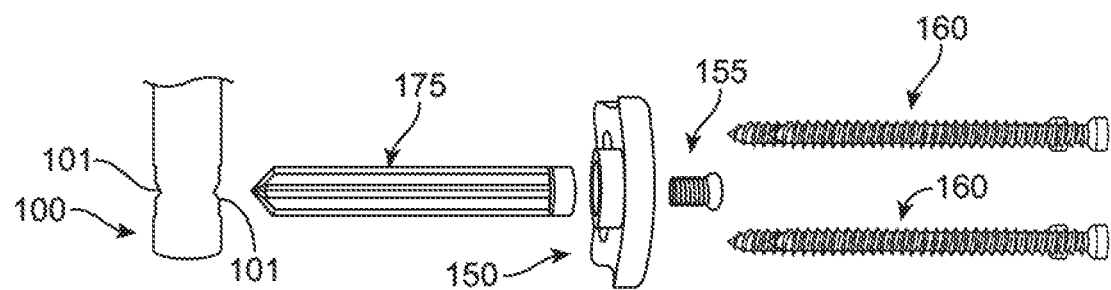
FIG. 3A is a top view depicting one end of an intramedullary rod, with the interlocking blade, intramedullary rod plate, plate securing device, and plate screws in an assembling position, in accordance with illustrative embodiments.
Figure 3B:
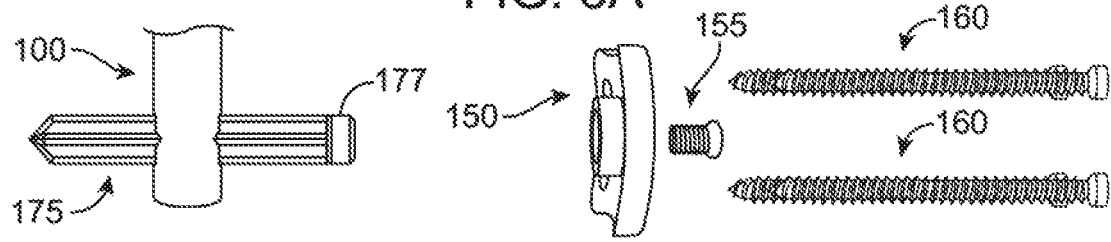
FIG. 3B is a top view depicting the interlocking blade inserted into the intramedullary rod, with the intramedullary rod plate, plate securing device, and plate screws in an assembling position, in accordance with illustrative embodiments.

Now turning to FIG. 3B, a top view depicting one end of intramedullary rod 100 now with interlocking blade 175 inserted through hole 101 (from FIG. 3A) is shown, in accordance with an illustrative embodiment. Interlocking blade 175 includes a head portion 177, as shown in FIG. 2B. Intramedullary rod plate 150, plate securing device 155, and plate screws 160 are shown in an assembling position, in accordance with illustrative embodiments.

Figure 3C:
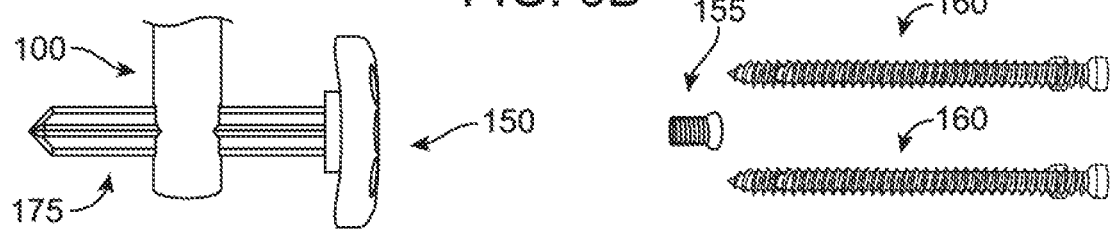
FIG. 3C is a top view depicting the intramedullary rod plate placed onto the interlocking blade that has been inserted into the intramedullary rod, with the plate securing device and plate screws in an assembling position, in accordance with illustrative embodiments.

Now turning to FIG. 3C, a top view depicting one end of intramedullary rod 100 with interlocking blade 175 inserted through hole 101 (from FIG. 3A), now with intramedullary rod plate 150 placed onto blade head portion 177 (from FIG. 3B) is shown, in accordance with an illustrative embodiment. Plate securing device 155 and plate screws 160 are shown in an assembling position, in accordance with illustrative embodiments.

Figure 3D:
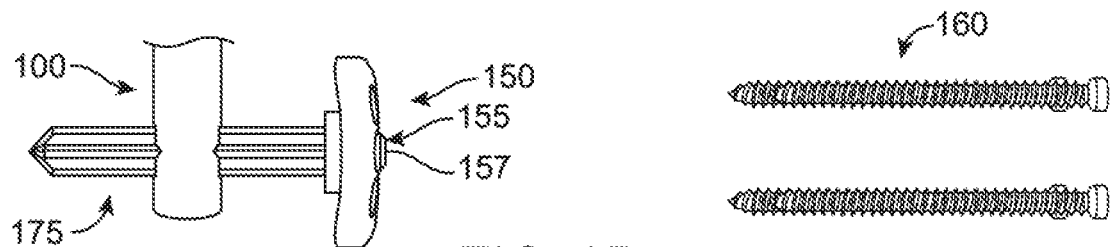
FIG. 3D is a top view depicting the plate securing device now securing the intramedullary rod plate to the interlocking blade that has been inserted into the intramedullary rod, with plate screws in an assembling position, in accordance with illustrative embodiments.

Now turning to FIG. 3D, a top view depicting one end of intramedullary rod 100 with interlocking blade 175 inserted through hole 101 (from. FIG. 3A) and intramedullary rod plate 150 placed onto blade head portion 177 (from FIG. 3B) is shown, in accordance with an illustrative embodiment. In FIG. 3D, the plate securing device 155 is shown securing interlocking blade 175 to intramedullary rod plate 150. It is noted that only the plate securing device head 157 is visible because it has been inserted into interlocking blade 175, a process that is illustrated with reference to FIGS. 4A-4C. Plate screws 160 are shown in an assembling position, in accordance with illustrative embodiments. FIGS. 4A-4C and FIGS. 5A-5B further depict the interaction amongst interlocking blade 175, intramedullary rod plate 150, and plate securing device 155.

Figure 3E:
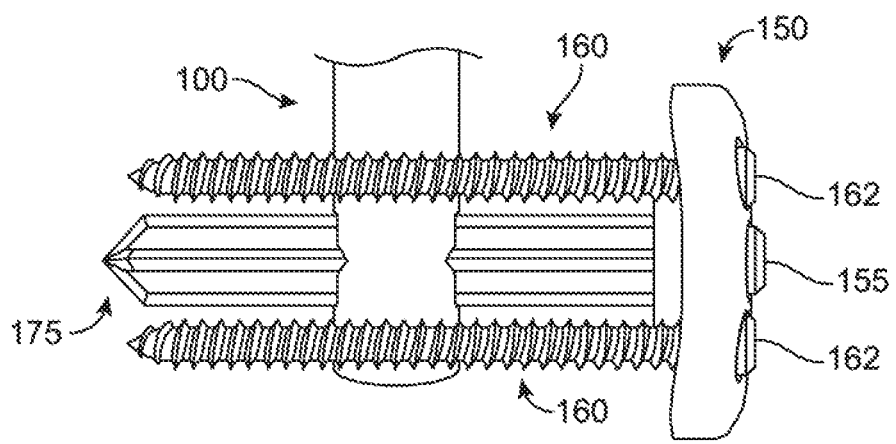
FIG. 3E is a top assembled view depicting the intramedullary rod plate secured to the interlocking blade that has been inserted into the intramedullary rod, in accordance with illustrative embodiments.

Now turning to FIG. 3E, a top view depicting an assembled intramedullary rod plate system is shown in accordance with an illustrative embodiment. The interlocking blade 175 is inserted through hole 101 (from FIG. 3A) in one end of intramedullary rod 100 and intramedullary rod plate 150 is placed onto blade head portion 177 (from FIG. 3B) of interlocking blade 175. The plate securing device 155 (only the plate securing device head 157 is visible) secures the interlocking blade 175 to intramedullary rod plate 150, now with plate screws 160 passed through intramedullary rod plate 150.

Figure 4C:
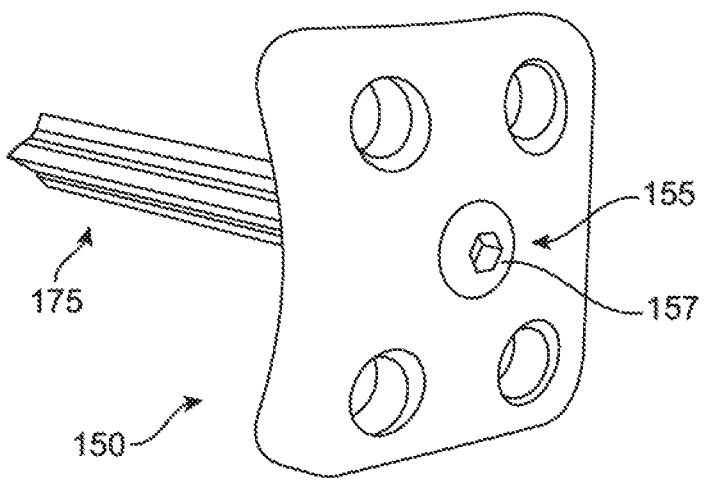
FIG. 4C is a perspective view depicting the assembled intramedullary rod plate secured to the interlocking blade with the plate securing device, in accordance with an illustrative embodiment.
Figure 5A:
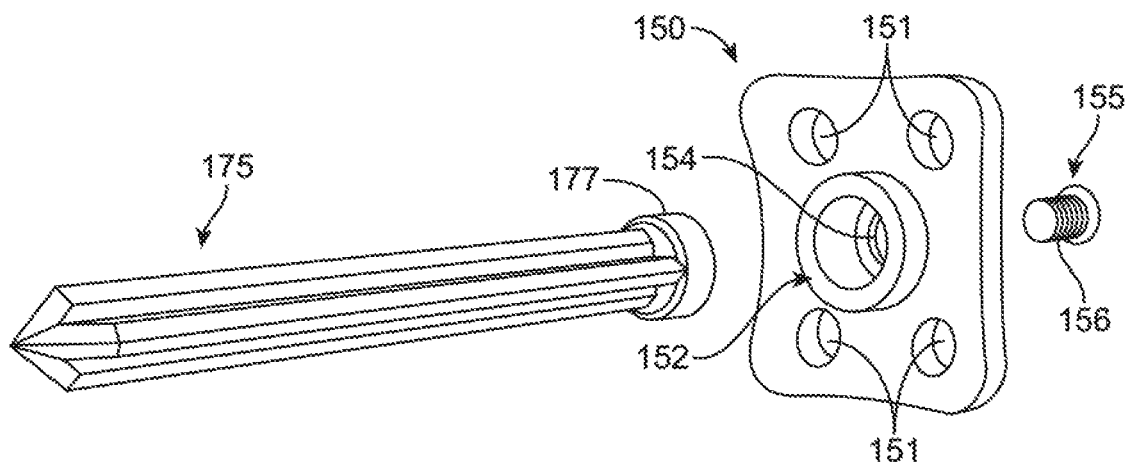
FIG. 5A is a perspective view depicting the interlocking blade, intramedullary rod plate, and plate securing device in an assembly position, in accordance with illustrative embodiments.
Figure 5B:
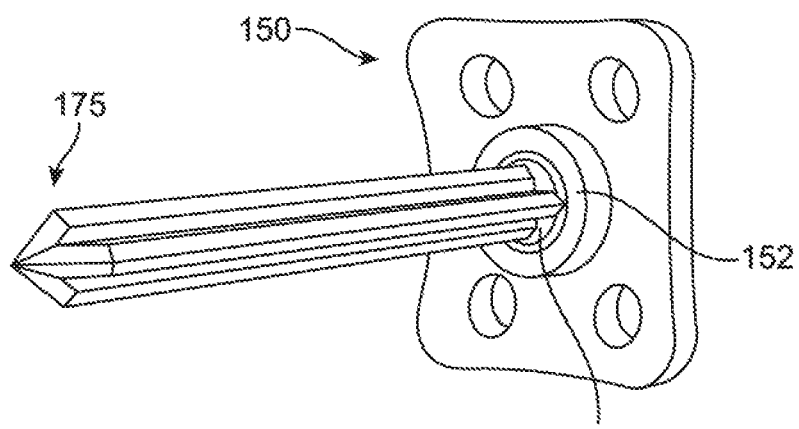
FIG. 5B is a perspective view depicting the intramedullary rod plate placed on the interlocking blade, in accordance with an illustrative embodiment.

FIGS. 4A-4C and FIGS. 5A-5B depict the assembly of interlocking blade 175 with intramedullary rod plate 150, in accordance with illustrative embodiments. FIGS. 4A-4C are views showing the lateral aspect, and FIGS. 5A-5B are views showing the medial aspect, of intramedullary rod plate 150. Turning now to FIG. 4A, a perspective view depicting interlocking blade 175, intramedullary rod plate 150, and plate securing device 155 in an assembly position is shown, in accordance with illustrative embodiments. In some embodiments, interlocking blade 175 includes a head portion 177 with a central threaded hole 178. Threaded hole 178 faces laterally and can accommodate and mate with the threaded shaft portion 156 of plate securing device 155. In some embodiments, intramedullary rod plate 150 includes four holes 151 that can accommodate plate screws (160, shown in FIG. 2B). In alternative embodiments, intramedullary rod plate 150 can include fewer or more than four holes 151 that can accommodate plate screws 160 or other fasteners. In some embodiments, intramedullary rod plate 150 can include a central cylindrical receiving part 152 (partially shown here, also shown in FIG. 2B, and later shown in FIG. 5A) that accommodates head portion 177 of interlocking blade 175 on the medial side of the plate. The intramedullary rod plate also includes a central plate hole 154 that allows for passage of threaded shaft portion 156 of plate fastener 155 through intramedullary rod plate 150 into threaded portion 178 of interlocking blade 175. In some embodiments, central hole 154 can include a side wall 153 that faces substantially lateral and accommodates the medial plate-facing surface of plate securing device head 157 of plate securing device 155. The relationship of these elements is further depicted in FIGS. 4B-4C.

Now turning to FIG. 4B, a perspective view depicting intramedullary rod plate 150 seated on interlocking blade 175, with plate securing device 155 in an assembly position is shown, in accordance with illustrative embodiments. Threaded hole 178 (see also FIG. 4A) of interlocking blade 175 is visible through central plate hole 154 and in some embodiments is configured to mate with the threaded shaft portion 156 of plate securing device 155.

Now turning to FIG. 4C, a perspective assembled view depicting intramedullary rod plate 150 secured to interlocking blade 175 with plate securing device 155 is shown, in accordance with an illustrative embodiment. In FIG. 4C, only the plate securing device head 157 is visible because the threaded shaft portion 156 from FIGS. 4A and 4B has been inserted into threaded hole 178 from FIGS. 4A and 4B.

Turning now to FIG. 5A, a perspective view depicting interlocking blade 175, intramedullary rod plate 150, and plate securing device 155 in an assembly position is shown, in accordance with illustrative embodiments. In some embodiments, interlocking blade 175 can include a head portion 177, with a central threaded hole 178 (not shown here, shown in FIGS. 4A and 4B) that accepts and mates with the threaded shaft portion 156 of plate securing device 155. In some embodiments, intramedullary rod plate 150 includes four holes 151 that can accommodate plate screws 160 (from FIG. 2B) or other fasteners. In alternative embodiments, intramedullary rod plate 150 can include fewer or more than four holes 151 that can accommodate plate screws 160 (from FIG. 2B) or other fasteners. In some embodiments, intramedullary rod plate 150 includes a central cylindrical receiving part 152 (also shown in FIG. 28 and partially shown in FIG. 4A) that accommodates head portion 177 of interlocking blade 175, and an intramedullary-rod plate hole 154 that allows passage of threaded shaft portion 156 through intramedullary rod plate 150 into threaded portion 178 (from FIGS. 4A and 4B) of interlocking blade 175. In alternative embodiments, cylindrical receiving part 152 and intramedullary rod plate hole 154 may be eccentrically located in an intramedullary rod plate, rather than centrally located. In alternative embodiments, there may be more than one eccentrically-located cylindrical receiving part 152 and corresponding intramedullary rod plate hole 154, in which system there would be two or more sites of attachment of an intramedullary rod plate to an intramedullary rod via two or more interlocking blades or other fasteners.

Turning now to FIG. 5B, a perspective assembled view depicting intramedullary rod plate 150 secured to interlocking blade 175 with plate securing device 155 (from FIG. 5A) is shown, in accordance with an illustrative embodiment. Interlocking blade head 177 is shown seated in cylindrical receiving part 152.

Figure 6A:
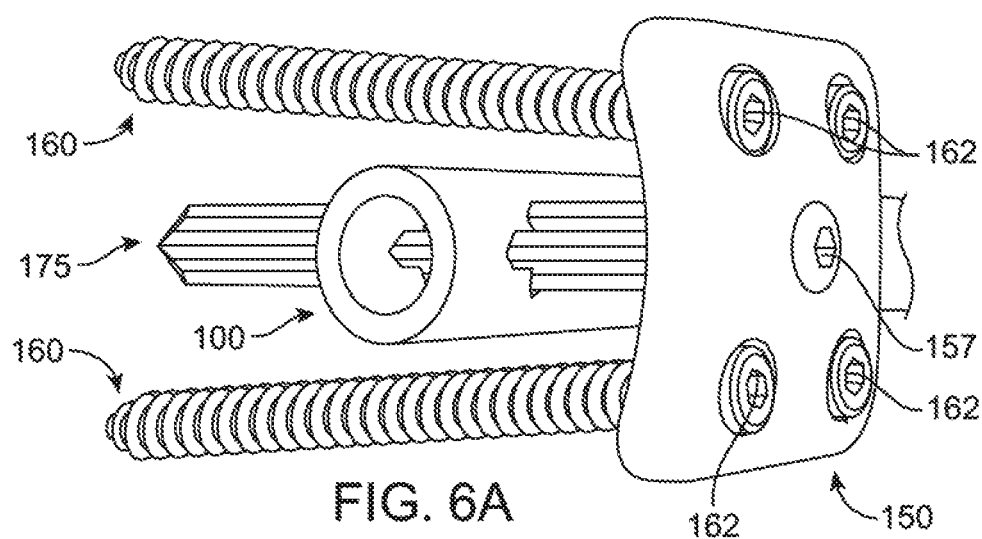
FIG. 6A is a first perspective view depicting the assembled intramedullary rod plate secured to the interlocking blade that has been inserted into the intramedullary rod, with plate screws placed through the intramedullary rod plate, in accordance with an illustrative embodiment.
Figure 6B:
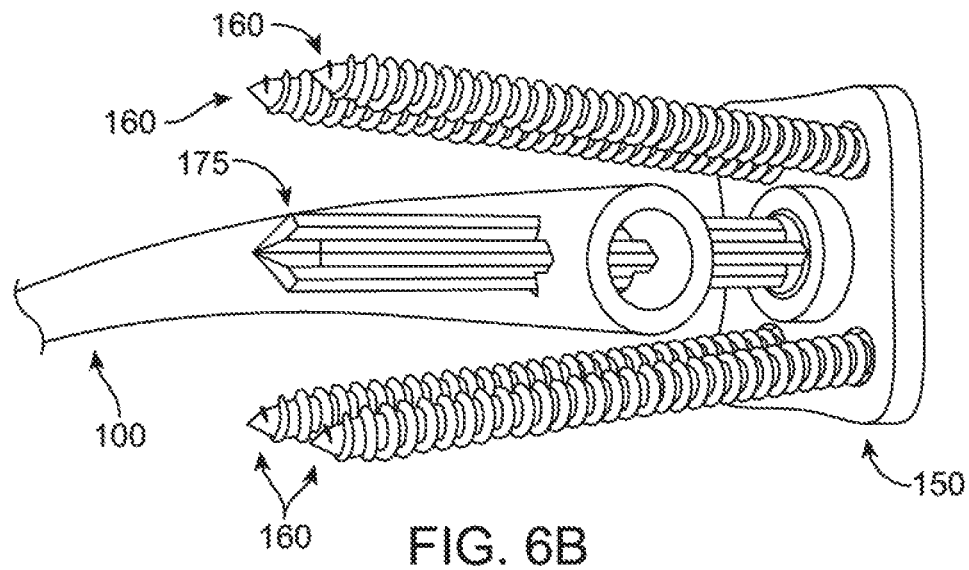
FIG. 6B is a second perspective view depicting the assembled intramedullary rod plate secured to the interlocking blade that has been inserted into the intramedullary rod, with plate screws placed through the intramedullary rod plate, in accordance with an illustrative embodiment.
Figure 6C:
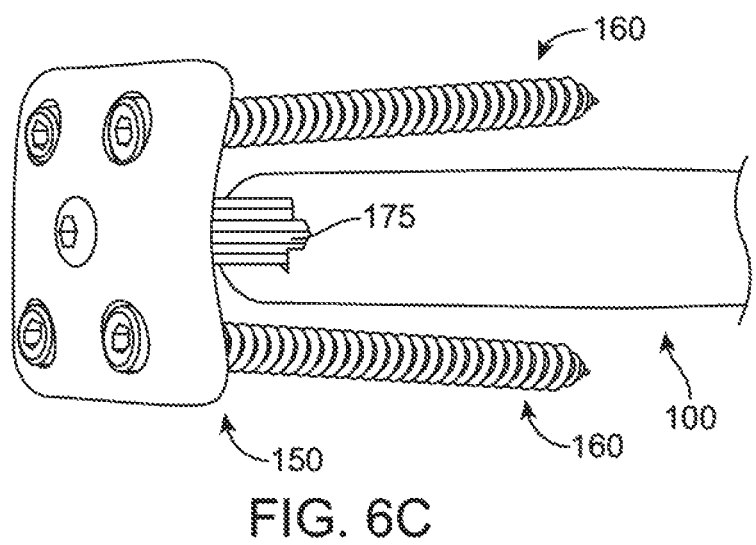
FIG. 6C is a third perspective view depicting the assembled intramedullary rod plate secured to the interlocking blade that has been inserted into the intramedullary rod, with plate screws placed through the intramedullary rod plate, in accordance with an illustrative embodiment.

FIGS. 6A-6C are perspective views depicting the assembled intramedullary rod plate system, with intramedullary rod plate 150 secured to interlocking blade 175 that has been inserted through intramedullary rod 100, with plate screws 160 placed through intramedullary rod plate 150, in accordance with illustrative embodiments. Turning now to FIG. 6A, a perspective view depicting the assembled intramedullary rod plate system is shown, in accordance with an illustrative embodiment. Intramedullary rod plate 150 is secured to interlocking blade 175 that has been inserted through hole 101 (from FIG. 3A) in intramedullary rod 100, with plate screws 160 placed through holes 151 (from FIGS. 4A and 5A) in intramedullary rod plate 150. Plate screw heads 162 are depicted pressing into the screw holes 151 (from FIGS. 4A and 5A) of intramedullary rod plate 150. Plate fixation device head 157 is shown, representing plate fixation device 155 (from FIGS. 4A, 4B, and 5A) securing intramedullary rod plate 150 to interlocking blade 175. The perspective view in FIG. 6A depicts the lateral face of intramedullary rod plate 150.

Turning now to FIG. 6B, a perspective view depicting the assembled intramedullary rod plate system is shown, in accordance with an illustrative embodiment. Intramedullary rod plate 150 is secured to interlocking blade 175 that has been inserted through hole 101 (from FIG. 3A) in intramedullary rod 100, with plate screws 160 placed through the intramedullary rod plate 150. The perspective view in FIG. 6B depicts the medial face of intramedullary rod plate 150.

Turning now to FIG. 6C, a perspective view depicting the assembled intramedullary rod plate system is shown, in accordance with an illustrative embodiment. Intramedullary rod plate 150 is secured to interlocking blade 175, which has been inserted through hole 101 (from FIG. 3A) in intramedullary rod 100, with plate screws 160 placed through intramedullary rod plate 150. The perspective view in FIG. 6C depicts the lateral face of intramedullary rod plate 150 as in FIG. 6A, but from a different perspective as in FIG. 6A.

Figure 7A:
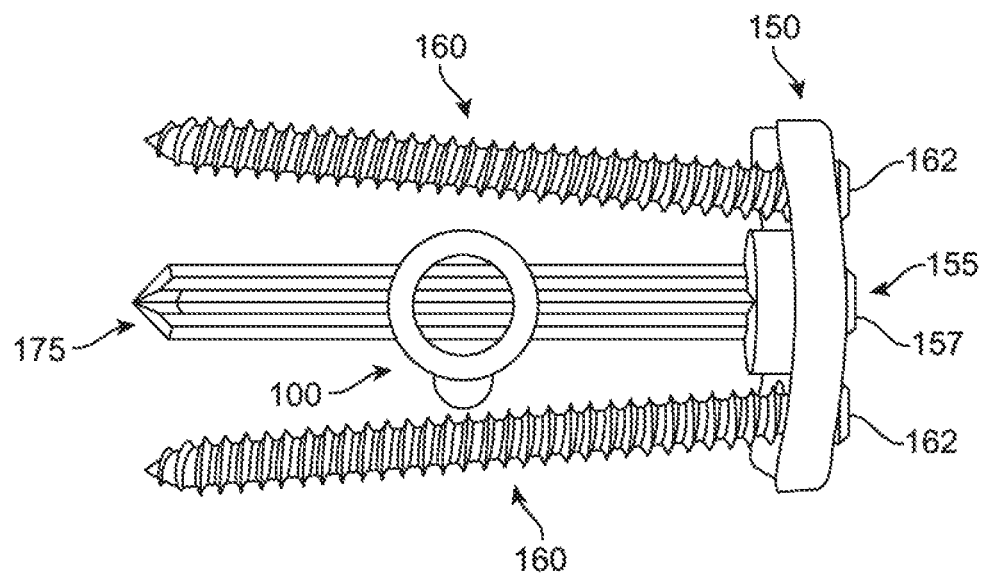
FIG. 7A is an end view depicting the assembled intramedullary rod plate secured to the interlocking blade that has been inserted into the intramedullary rod, in accordance with an illustrative embodiment.

Turning now to FIG. 7A, an end view depicting the assembled intramedullary rod plate system is shown, in accordance with an illustrative embodiment. Intramedullary rod plate 150 is secured to interlocking blade 175 with plate securing device 155 (partially shown as represented by plate seeming device head 157) interlocking blade 175 has been inserted through hole 101 (from FIG. 3A) in intramedullary rod 100, with plate screws 160 placed through the intramedullary rod plate 150. Plate screw heads 162 and plate securing device head 157 are partially visualized, having been inserted into and pressing against their respective holes in intramedullary rod plate 150.

Figure 7B:
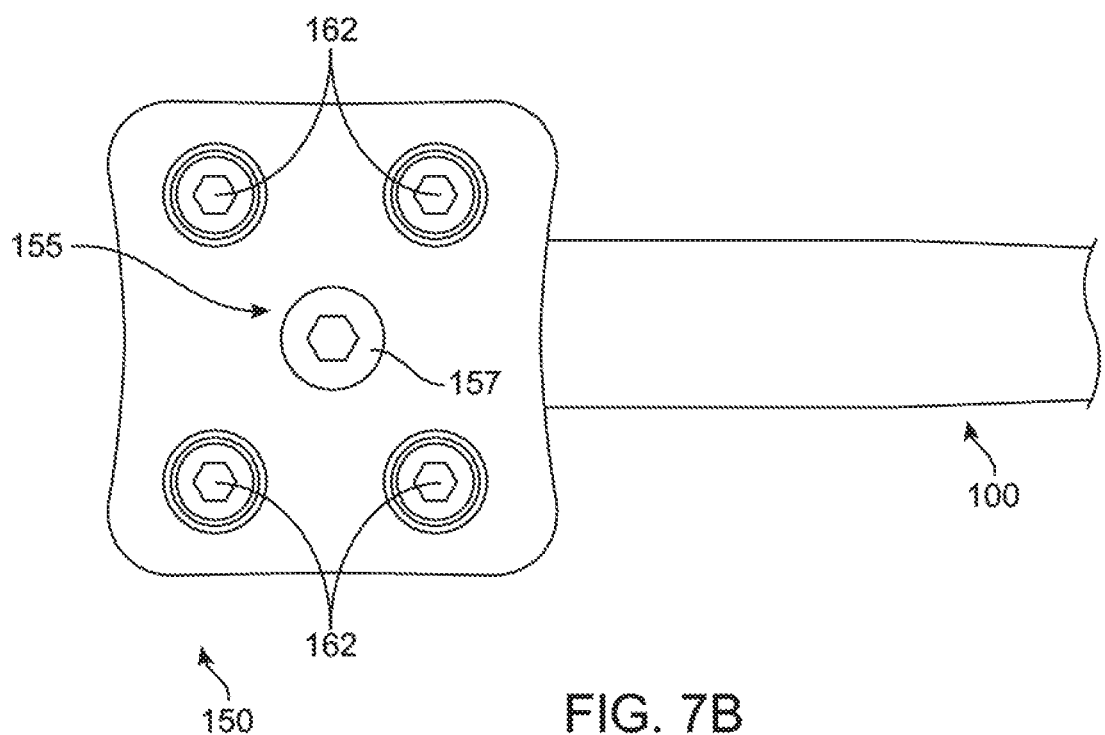
FIG. 7B is a side or lateral view depicting the assembled intramedullary rod plate with the plate securing device that attaches the intramedullary rod plate to the interlocking blade that has been inserted into the intramedullary rod, in accordance with an illustrative embodiment.

Turning now to FIG. 7B, a side or lateral view depicting the assembled intramedullary rod plate system is shown, in accordance with an illustrative embodiment Intramedullary rod plate 150 is secured to interlocking blade 175 (blade 175 not seen in this view because it is obscured by plate 150, see FIG. 7A) with plate securing device 155 (partially shown as represented by plate securing device head 157). Interlocking blade 175 has been inserted through hole 101 (from FIG. 3A) in intramedullary rod 100 (not seen in this view, see FIGS. 6A-6C and 7A), with plate screws 160 (not seen in this view because they are obscured by plate 150) represented by the visible plate screw heads 162 placed through their corresponding holes in intramedullary rod plate 150.

Figure 8A:
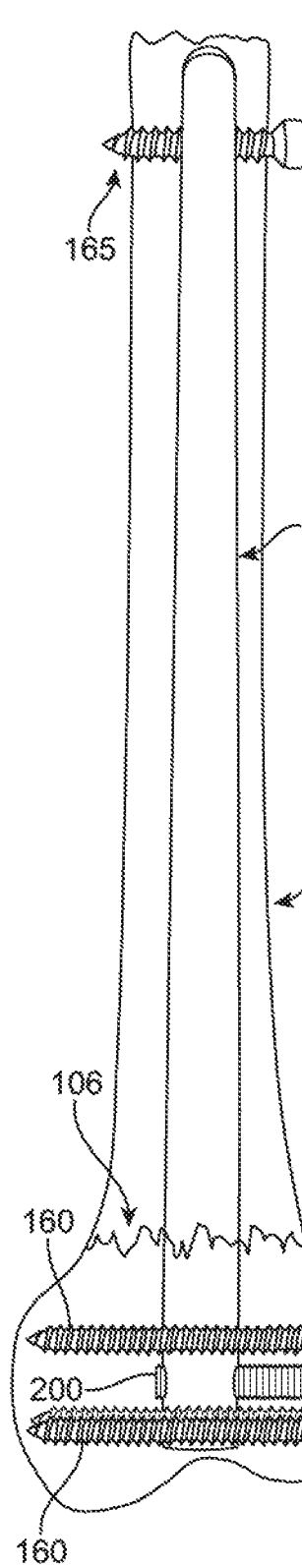
FIG. 8A is a top or anterior view depicting an intramedullary rod after insertion into a femur, with an interlocking bolt fastener inserted through the lateral aspect of the distal end of the femur and into the rod, and the intramedullary rod plate being attached to the bolt fastener, in accordance with an illustrative embodiment. The intramedullary rod plate is attached to the interlocking bolt fastener, and plate screws have been inserted into the distal end of the femur through holes in the intramedullary rod plate, thus securing the intramedullary rod plate to the distal end of the femur.
Figure 8B:
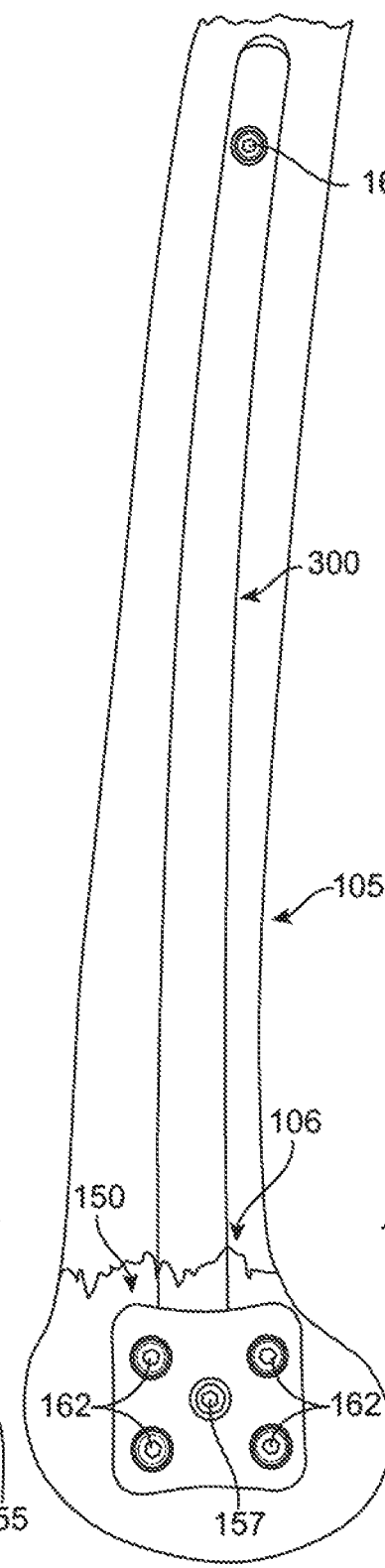
FIG. 8B is a side or lateral view depicting an intramedullary rod after insertion into a femur, with an interlocking bolt fastener (not shown) inserted through the lateral aspect of the distal end of the femur and into the rod, and the intramedullary rod plate is attached to the bolt fastener not shown), in accordance with an illustrative embodiment. The intramedullary rod plate is attached to the interlocking bolt fastener (not shown) with the plate securing device, and plate screws have been inserted into the distal end of the femur through holes in the intramedullary rod plate, thus securing the intramedullary rod plate to the distal end of the femur. In this depiction, the terminal ends of the plate screws are not visualized because they are depicted as having been placed perpendicular to the lateral plate surface, thus hidden from view by the plate when viewed from the side.
Figure 8C:
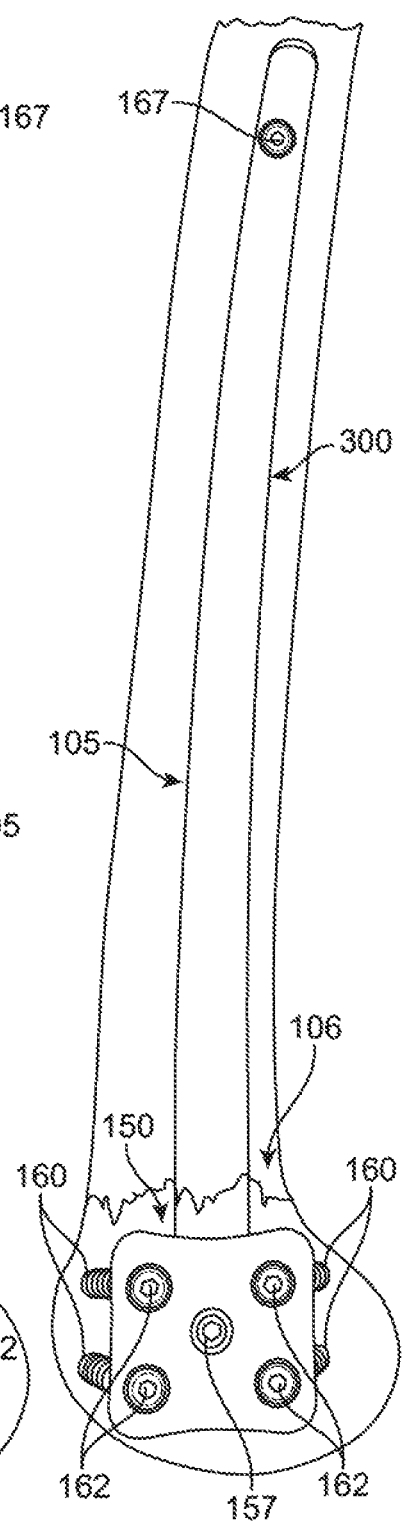
FIG. 8C is a side or lateral view depicting an intramedullary rod after insertion into a femur, with an interlocking bolt fastener (not shown) inserted through the lateral aspect of the distal end of the femur and into the rod, and the intramedullary rod plate is attached to the bolt fastener not shown), in accordance with an illustrative embodiment. The intramedullary rod plate is attached to the interlocking bolt fastener (not shown) with the plate securing device, and plate screws have been inserted into the distal end of the femur through holes in the intramedullary rod plate, thus securing the intramedullary rod plate to the distal end of the femur. In this depiction, the terminal ends of the plate screws are visualized because they are depicted as having been placed obliquely to the lateral plate surface, divergent from the long axis of the intramedullary rod.

FIGS. 8A-8C depict an alternative embodiment of the intramedullary rod plate system. In this embodiment, a threaded interlocking bolt fastener (rather than an interlocking blade fastener as depicted in FIGS. 1-7) is used to attach an intramedullary rod plate to an intramedullary rod. Turning now to FIG. 8A, a top or anterior view depicting the intramedullary rod plate system in an assembled position is shown, in accordance with an illustrative embodiment. In some embodiments, the intramedullary rod plate system includes intramedullary rod plate 150, plate screws 160, and plate securing device 155 (partially shown) that secures intramedullary rod plate 150 to threaded interlocking bolt fastener 200 (henceforth referred to as an interlocking bolt 200). Intramedullary rod 300 has been inserted in a retrograde fashion into the intramedullary canal of femur 105 in order to stabilize distal femur fracture 106. Fracture fixation distal to the fracture occurs by transferring the bone fixation force achieved with screws 160 (that are inserted into distal femur bone) to intramedullary rod plate 150, which in turn transfers this force to the intramedullary rod 300 through the attachment of interlocking bolt 200 to both the intramedullary rod plate 150 and intramedullary rod 300. In comparison to the intramedullary rod plate system depicted in FIG. 1A, FIG. 8A depicts an interlocking bolt 203 that extends through a corresponding hole in intramedullary rod 300 by just enough length, approximately 2-5 millimeters, to secure bolt 200 to rod 300. In contradistinction to the interlocking blade 175 that may have a frictional fit with bone and provide some stability as described in FIG. 1A, interlocking bolt 200 would not be expected to have a significant frictional fit with bone and therefore would not be expected to itself confer additional stability to the fixation construct. Instead, interlocking bolt 200 would be expected to serve predominantly as a method of attachment of intramedullary rod plate 150 to intramedullary rod 300. In alternative embodiments, interlocking bolt 200 may be configured to extend a similar distance through intramedullary rod 300 as interlocking blade 175 (from FIG. 1A) and achieve some frictional fit with bone, thereby imparting some additional stability to the fixation construct.

Intramedullary rod fixation proximal to the fracture occurs via the frictional fit of the outer surface of intramedullary rod 300 to the surface of the medullary canal of femur 105. This proximal fixation may be augmented by placing interlocking screws 165 or fasteners through bone located towards the proximal end of the femur and through holes in the intramedullary rod 300 at the end of the intramedullary rod opposite the end of the rod with interlocking bolt 200 (e.g., proximal the interlocking screws).

Referring now to FIG. 8B in conjunction with FIG. 8A, a side or lateral view depicting the intramedullary rod plate system in an assembled position after retrograde insertion of the intramedullary rod 300 into the intramedullary canal of a femur 105 in order to stabilize distal femur fracture 106 is shown, in accordance with an illustrative embodiment. Intramedullary rod plate 150 is secured to interlocking bolt 200 (shown in FIG. 8A but not seen in FIG. 8B) by plate securing device 155 (partially shown, the head 157 of plate securing device 155 is shown here). In some embodiments, intramedullary rod plate 150 can include four holes to accommodate four plate screws 160 (not shown, plate screw heads 162 are shown here, representing plate screws 160 as seen in FIG. 8A). In alternative embodiments, intramedullary rod plate 150 can include more or fewer holes and can thus be used with more or fewer than four plate screws 160. In some embodiments, intramedullary rod plate 150 may be pre-contoured or contoured intra-operatively to closely match the local bony anatomy. In this depiction, the terminal ends of the plate screws 160 (not shown here, shown in FIGS. 8A and 8C) are not visualized because they are depicted as having been placed perpendicular to the lateral intramedullary rod plate surface, and so are hidden in this view by intramedullary rod plate 150.

Intramedullary rod fixation proximal to the fracture occurs via the frictional fit of the outer surface of the intramedullary rod 300 to the surface of the medullary canal of femur 105. This proximal fixation may be augmented by placing one or more interlocking screws 165 (as represented in this view by interlocking screw head 167) or fasteners through bone located towards the proximal end of the femur. The one or more interlocking screws or fasteners are also placed through a hole or holes in the intramedullary rod 300 at the end of the intramedullary rod opposite the end of the rod with interlocking bolt 200 (e.g., proximal the interlocking screws).

Referring now to FIG. 8C in conjunction with FIGS. 8A and 8B, a side or lateral view depicting the intramedullary rod plate system in an assembled position after retrograde insertion of the intramedullary rod 300 into the intramedullary canal of the femur 105 in order to stabilize distal femur fracture 106 is shown, in accordance with an illustrative embodiment. Intramedullary rod plate 150 is secured to interlocking bolt 200 (shown in FIG. 8A but not seen in FIG. 8C) by plate securing device 155 (partially shown, the head 157 of plate securing device 155 is shown here). In some embodiments, intramedullary rod plate 150 can include four holes to accommodate four plate screws 160. In alternative embodiments, intramedullary rod plate 150 can include more or fewer holes and can thus be used with more or fewer than four plate screws 160. In some embodiments, intramedullary rod plate 150 may be pre-contoured or contoured intra-operatively to closely match the local bony anatomy. In this depiction, the terminal ends of the plate screws 160 are visualized because they are shown as having been placed obliquely to the lateral intramedullary rod plate surface, divergent from the long axis of the intramedullary rod. The anterior-posterior and cephalad-caudal angle at which screws 160 can be inserted is determined by the surgeon according to available intact femoral bone that can be employed to achieve screw 160 purchase. The anterior-posterior and cephalad-caudal angle at which screws 160 can be inserted has many degrees of freedom and is not limited by being required to pass through holes in intramedullary rod 300, as is the case with conventional intramedullary rod systems. Plate screw heads 162, which are part of plate screws 160, are shown, as in FIG. 8B.

Figure 10A:
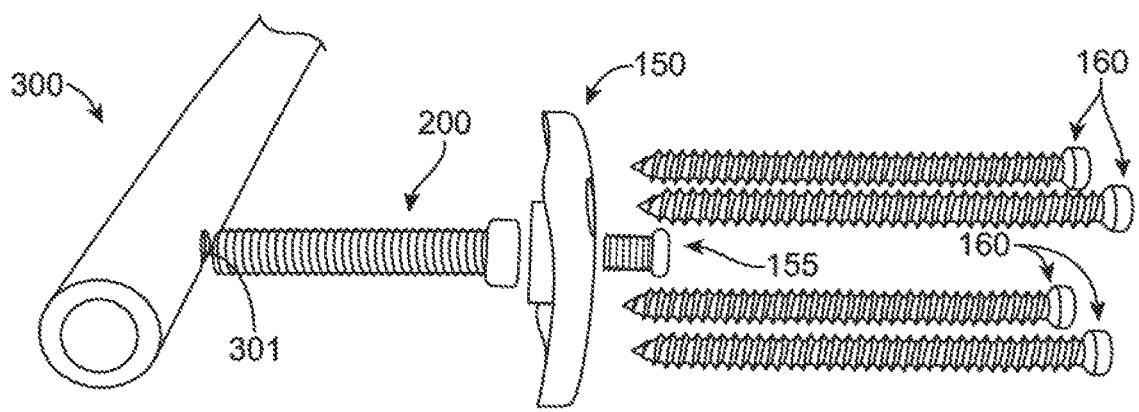
FIG. 10A is a perspective view depicting one end of an intramedullary rod, with interlocking bolt, intramedullary rod plate, plate securing device, and plate screws in an assembling position, in accordance with illustrative embodiments.

Turning now to FIG. 9A, a perspective view depicting the assembled intramedullary rod plate system is shown, in accordance with an illustrative embodiment. Intramedullary rod plate 150 is secured to interlocking bolt 200 that has been inserted through reciprocal threads in a hole 301 (see FIGS. 10A and 10B) in intramedullary rod 300, with plate screws 160 placed through intramedullary rod plate 150. The terminal end 200a of interlocking bolt 200 extends through intramedullary rod 300 just enough distance to ensure fixation of bolt 200 to rod 300. The bolt 200 does not have a frictional fit with distal femur bone, as is described with interlocking blade 175 in FIG. 1A. In some embodiments, interlocking bolt 200 serves predominantly as a method of attachment of intramedullary rod plate 150 to intramedullary rod 300. In alternative embodiments, interlocking bolt 200 may be configured to extend a similar distance through intramedullary rod 300 as interlocking blade 175 (from FIG. 1A) to achieve some frictional fit with bone, thereby imparting some additional stability to the fixation construct. Plate fixation device head 157 is shown, representing plate fixation device 155 as shown in FIGS. 9B and 9C, and used for securing intramedullary rod plate 150 to interlocking bolt 200.

FIGS. 9B-9E depict assembly of interlocking bolt 200 with intramedullary rod plate 150. Turning now to FIG. 9B, a perspective view depicting interlocking bolt 200, intramedullary rod plate 150, and plate securing device 155 in an assembly position are shown, in accordance with illustrative embodiments. In some embodiments, interlocking bolt 200 can include a threaded shaft portion 201, and a head portion 202 with a central threaded hole 203. In alternative embodiments, threaded shaft portion 201 can be configured as partially-threaded, with threads covering sufficient length to mate with reciprocal threads in a hole 301 (see FIGS. 10A and 10B) in intramedullary rod 300. Threaded hole 203 can accommodate and mate with the threaded shaft portion 156 of plate securing device 155. In some embodiments, intramedullary rod plate 150 includes four holes 151 that can accommodate plate screws (160, shown in FIG. 2B) or fasteners. In some embodiments, intramedullary rod plate 150 can include a central cylindrical receiving part 152 (partially shown here, also shown in FIG. 2B and FIG. 5A and later in FIG. 9D) that accommodates head portion 202 of interlocking bolt 200 on the medial side of the plate. The lateral side of the plate 150 is shown here, the medial side of the plate 150 is shown in FIG. 9D. The intramedullary rod plate 150 also includes a plate hole 154 that allows for passage of threaded shaft portion 156 of plate fastener 155 through intramedullary rod plate 150 into threaded portion 203 of interlocking bolt 200. In some embodiments, central hole 154 can include a laterally-facing side wall 153 that accommodates the plate-facing medial surface of plate securing device head 157 of plate securing device 155.

Now turning to FIG. 9C, a perspective assembled view depicting intramedullary rod plate 150 secured to interlocking bolt 200 with plate securing device 155 (only the plate securing device head 157 is visible) is shown, in accordance with an illustrative embodiment.

Now turning to FIG. 9D, a perspective view depicting interlocking bolt 200, intramedullary rod plate 150, and plate securing device 155 in an assembly position are shown, in accordance with illustrative embodiments. FIG. 9B shows the lateral face of intramedullary rod plate 150 and the relative configurations of interlocking bolt 200 and plate securing device 155, whereas FIG. 9D shows the medial face of intramedullary rod plate 150 and the relative configurations of interlocking bolt 200 and plate securing device 155. In some embodiments, interlocking bolt 200 can include a head portion 202, with a central threaded hole 203

(not shown here, shown in FIG. 9B) that mates with threaded shaft portion 156 of plate securing device 155. In some embodiments, intramedullary rod plate 150 includes four holes 151 that can accommodate plate screws 160 (from FIG. 9A). In alternative embodiments, intramedullary rod plate 150 can include fewer or more than four holes 151 that can accommodate plate screws 160 or other fasteners. In some embodiments, intramedullary rod plate 150 includes a central cylindrical receiving part 152 (also shown in FIG. 2B and partially shown in FIG. 4A and FIG. 9B) that accommodates head portion 202 of interlocking bolt 200. The intramedullary rod plate 150 also includes an intramedullary rod plate hole 154 that allows passage of threaded shaft portion 156 of plate fastener 155 through intramedullary rod plate 150 into threaded portion 203 (not shown here, shown in FIG. 9B) of interlocking bolt 200. In alternative embodiments, cylindrical receiving part 152 and intramedullary rod plate hole 154 may be eccentrically located in an intramedullary rod plate, rather than centrally located. In alternative embodiments, cylindrical receiving part 152 and intramedullary rod plate hole 154 may be eccentrically located in an intramedullary rod plate, rather than centrally located. In alternative embodiments, there may be more than one eccentrically-located cylindrical receiving part 152 and corresponding intramedullary rod plate hole 154, in which system there would be two or more sites of attachment of an intramedullary rod plate to an intramedullary rod via two or more interlocking bolts.

Turning now to FIG. 9E, a perspective assembled view depicting intramedullary rod plate 150 secured to interlocking bolt 200 with plate securing device 155 (not seen here, shown in FIG. 9B) is shown, in accordance with an illustrative embodiment. Interlocking bolt head 202 is shown seated in cylindrical receiving part 152. FIG. 9C shows the lateral face of intramedullary rod plate 150 and the relative configurations of interlocking bolt 200 and plate securing device head 157, whereas FIG. 9E shows the medial face of intramedullary rod plate 150 and the relative configuration of interlocking bolt 200 (plate securing device 155 and plate securing device head 157 are not seen in this view).

FIGS. 10A-10D depict the assembly sequence of an embodiment of the intramedullary rod plate system. Now turning to FIG. 10A, a top view depicting one end of intramedullary rod 300, with interlocking bolt 200, intramedullary rod plate 150, plate securing device 155, and plate screws 160 are shown in an assembling position, in accordance with illustrative embodiments. Intramedullary rod 300 includes a threaded hole 301 (partially shown) that accommodates and fastens to the threads of interlocking bolt 200. In an alternative embodiment, hole 301 may not be threaded.

Figure 10B:
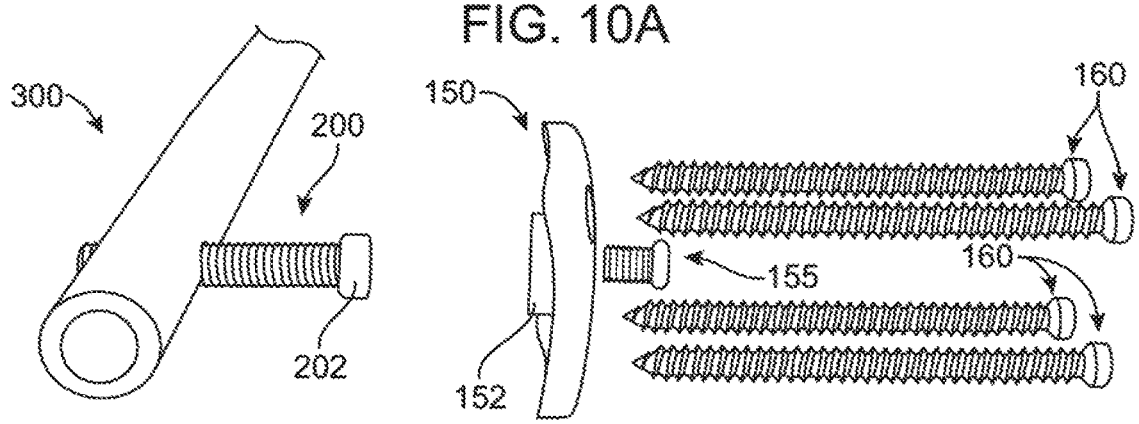
FIG. 10B is a perspective view depicting the interlocking bolt inserted into the intramedullary rod, with the intramedullary rod plate, plate securing device, and plate screws in an assembling position, in accordance with illustrative embodiments.

Now turning to FIG. 10B, a top view depicting one end of intramedullary rod 300 now with interlocking bolt 200 threaded through hole 301 (from FIG. 10A) is shown, in accordance with an illustrative embodiment. Interlocking bolt 200 includes a head portion 202, as also shown in FIGS. 9B and 9D, which fits into cylindrical receiving part 152 (partially shown here, more fully shown in FIG. 9D). Intramedullary rod plate 150, plate securing device 155, and plate screws 160 are shown in an assembling position, in accordance with illustrative embodiments.

Figure 10C:
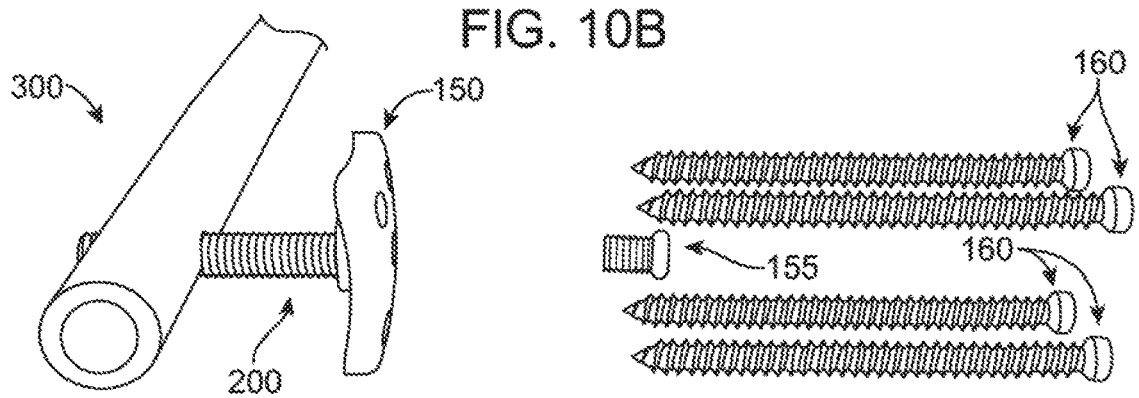
FIG. 10C is a perspective view depicting the intramedullary rod plate placed onto the interlocking bolt that has been inserted into the intramedullary rod, with the plate securing device and plate screws in an assembling position, in accordance with illustrative embodiments.

Now turning to FIG. 10C, a top view depicting one end of intramedullary rod 300 with interlocking bolt 200 threaded through hole 301 (from FIG. 10A), now with intramedullary rod plate 150 placed onto interlocking bolt head portion 202 (from FIG. 10B) is shown, in accordance with an illustrative embodiment. Plate securing device 155 and plate screws 160 are shown in an assembling position, in accordance with illustrative embodiments.

Figure 10D:
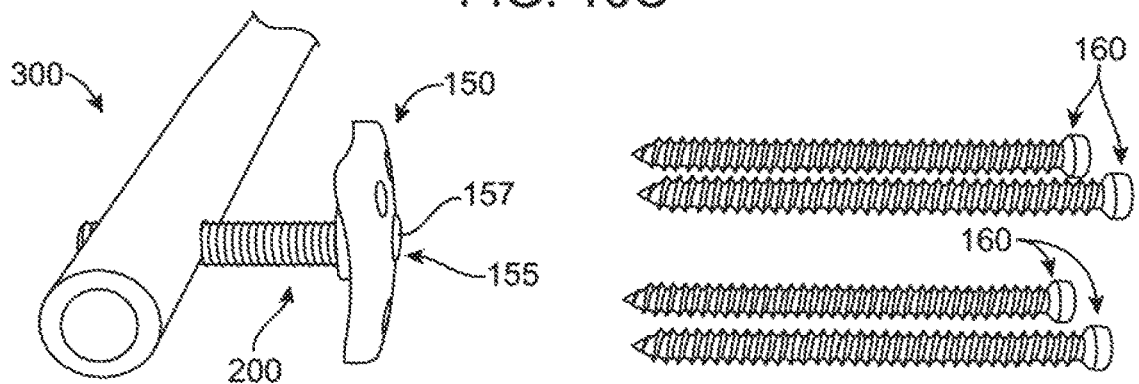
FIG. 10D is a perspective view depicting the plate securing device now securing the intramedullary rod plate to the interlocking bolt that has been inserted into the intramedullary rod, with plate screws in an assembling position, in accordance with illustrative embodiments.
Figure 11A:
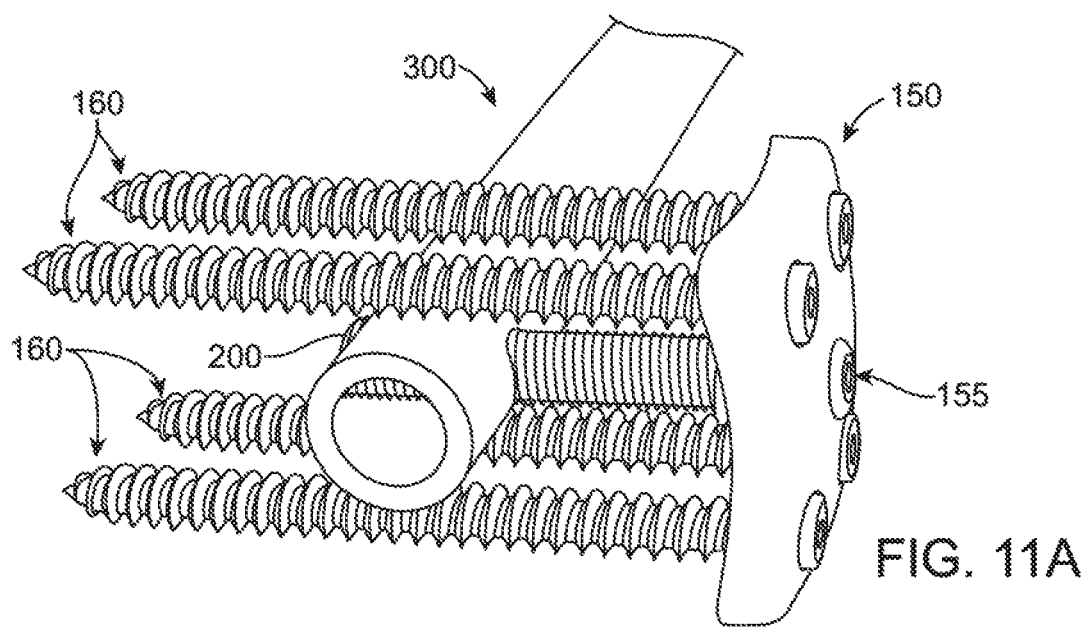
FIG. 11A is a perspective view depicting the assembled plate securing device securing the intramedullary rod plate to the interlocking bolt that has been inserted into the intramedullary rod, with plate screws inserted through the intramedullary rod plate, in accordance with an illustrative embodiment.
Figure 11B:
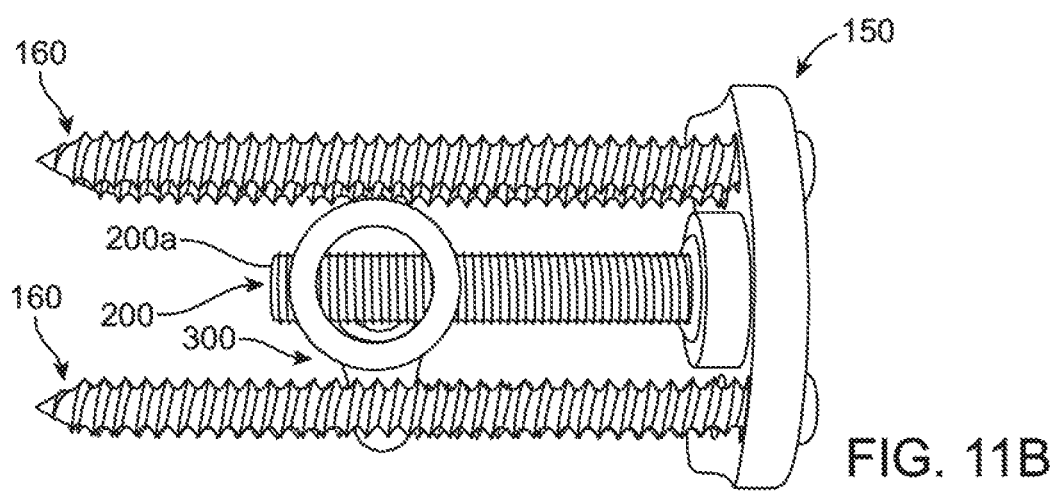
FIG. 11B is an end view depicting the assembled intramedullary rod plate secured to the interlocking bolt that has been inserted into the intramedullary rod, with plate screws inserted through the intramedullary rod plate, in accordance with an illustrative embodiment.
Figure 11C:
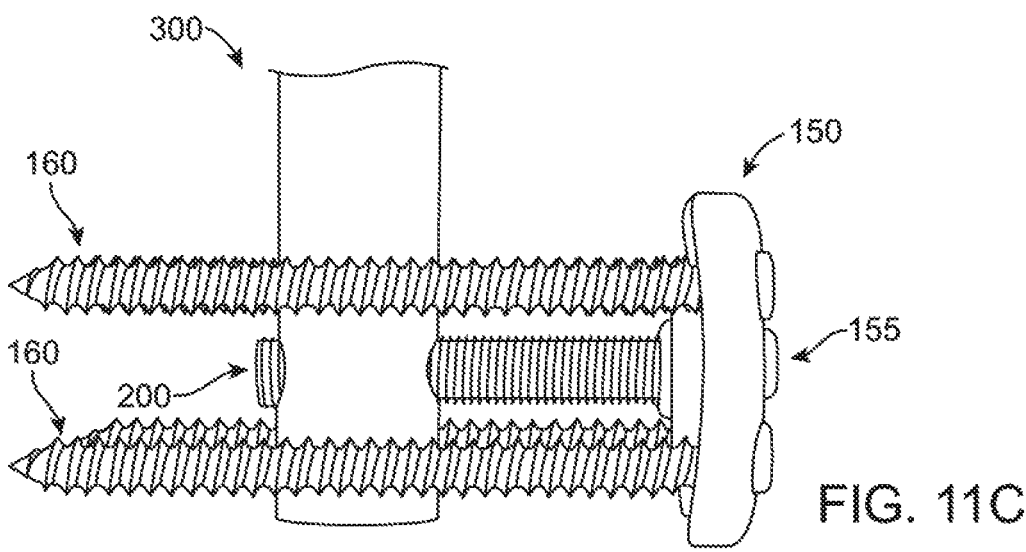
FIG. 11C is a top view depicting the assembled plate securing device securing the intramedullary rod plate to the interlocking bolt that has been inserted into the intramedullary rod, with plate screws inserted through the intramedullary rod plate, in accordance with an illustrative embodiment.

Now turning to FIG. 10D, a top view depicting one end of intramedullary rod 300 with interlocking bolt 200 threaded through hole 301 (from FIG. 10A) and intramedullary rod plate 150 placed onto interlocking bolt head portion 202 (from FIG. 10B) is shown in accordance with an illustrative embodiment. In FIG. 10D the plate securing device 155 (only the plate securing device head 157 is visible) secures interlocking bolt 200 to intramedullary rod plate 150. Plate screws 160 are shown in an assembling position, in accordance with an illustrative embodiment. FIGS. 11A-11C will further depict the interaction amongst interlocking bolt 200, intramedullary rod plate 150, and plate securing device 155.

FIGS. 11A-11C depict perspective views of one embodiment of the assembled intramedullary rod plate system, in accordance with an illustrative embodiment. Now turning to FIG. 11A, a perspective view depicting one end of intramedullary rod 300 with interlocking bolt 200 threaded through hole 301 (from FIG. 10A) and intramedullary rod plate 150 placed onto bolt head portion 202 (from FIG. 10B) and plate securing device 155 (only the plate securing device head, 157 from FIG. 9B, is visible) securing interlocking bolt 200 to intramedullary rod plate 150, with plate screws 160 passed through intramedullary rod plate 150 is shown, in accordance with an illustrative embodiment.

In FIG. 11B, an end view depicting intramedullary rod 300 with interlocking bolt 200 inserted through hole 301 (from FIG. 10A) and intramedullary rod plate 150 placed onto bolt head portion 202 (from FIG. 10B) is shown in accordance with an illustrative embodiment. The plate securing device 155 (not seen in this view) secures interlocking bolt 200 to intramedullary rod plate 150, and plate screws 160 pass through intramedullary rod plate 150. The terminal end 200a of interlocking bolt 200 extends through intramedullary rod 300 just enough distance to ensure fixation of bolt 200 to rod 300. The bolt 200 does not have a significant frictional fit with distal femur bone, as is described with interlocking blade 175 in FIG. 1A.

Now turning to FIG. 11C, a top view depicting one end of intramedullary rod 300 with interlocking bolt 200 inserted through hole 301 (from FIG. 10A) and intramedullary rod plate 150 placed onto bolt head portion 202 (from FIG. 10B) is shown in accordance with an illustrative embodiment. The plate securing device 155 (only the plate securing device head, 157 from FIG. 9B, is visible) secures interlocking bolt 200 to intramedullary rod plate 150, and plate screws 160 pass through intramedullary rod plate 150.

Figure 12A:
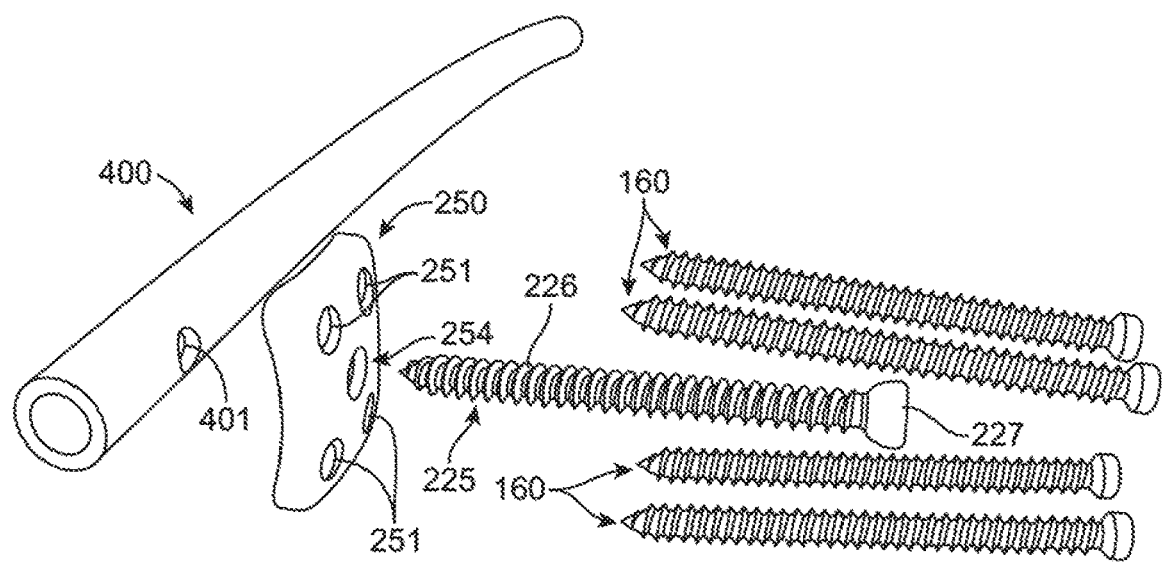
FIG. 12A is a perspective view depicting an intramedullary rod, with interlocking screw, intramedullary rod plate, and plate screws in an assembling position, in accordance with illustrative embodiments.
Figure 12B:
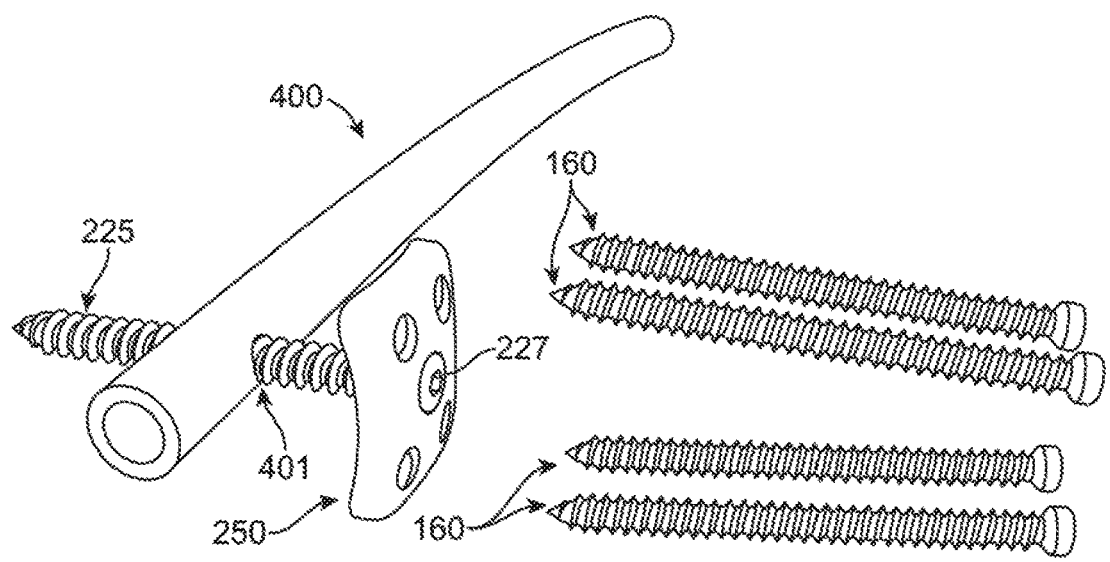
FIG. 12B is a perspective view depicting an interlocking screw passed through the intramedullary rod plate and the intramedullary rod, with plate screws in an assembling position, in accordance with illustrative embodiments.
Figure 12C:
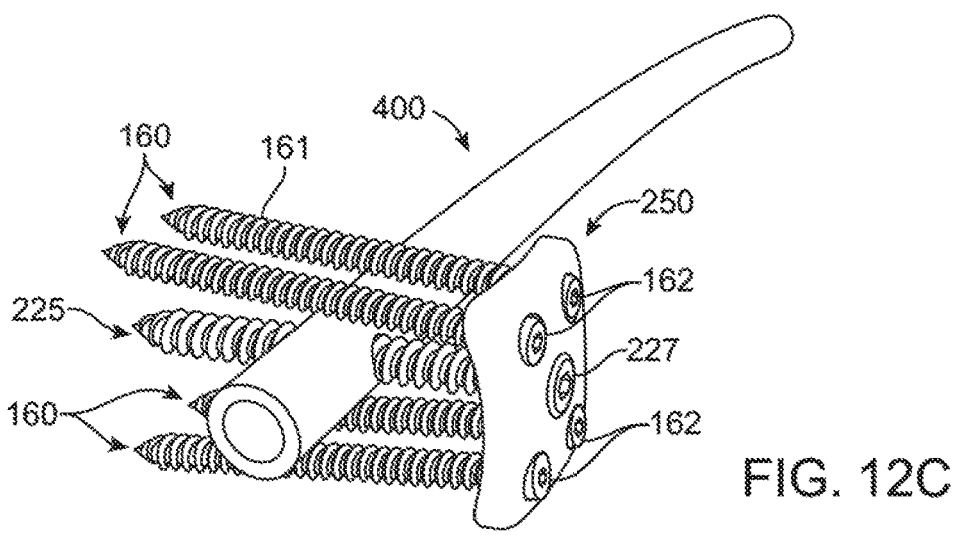
FIG. 12C is a perspective view depicting an assembled interlocking screw passed through the intramedullary rod plate and the intramedullary rod, with plate screws passed through the intramedullary rod plate, in accordance with an illustrative embodiment.

FIGS. 12A-12C depict the assembly sequence of an alternative embodiment of the intramedullary rod plate system. In this embodiment, an interlocking screw (rather than an interlocking blade as depicted in FIGS. 1-7, or an interlocking bolt as depicted in FIGS. 8-11) is used to attach an intramedullary rod plate to an intramedullary rod. Now turning to FIG. 12A, a perspective view depicting intramedullary rod 400, with interlocking screw fastener 225 (henceforth referred to as an interlocking screw 225), intramedullary rod plate 250, and plate screws 160 is shown in an assembling position, in accordance with illustrative embodiments. In some embodiments, interlocking screw 225 includes threaded shaft portion 226 and head portion 227. In alternative embodiments, interlocking fastener 225 may have a smooth or alternatively contoured surface that is configured to form a connection with rod 400. In some embodiments, intramedullary rod 400 includes a hole 401

(hole 401 on the lateral side of the rod is shown, and there is a corresponding hole directly opposite the visible hole 401, e.g., on the medial side of the rod) that accommodates interlocking screw 225. Hole 401 may include threads that mate with the threaded portion 226 of interlocking screw 225, or hole 401 may be thread-less, in which case in some embodiments the relationship between hole 401 and threaded shaft portion 226 creates an interference frictional fit between the threads of interlocking screw shaft 226 and the surface of hole 401. In some embodiments, intramedullary rod plate 250 includes four holes 251 that can accommodate plate screws 160. In alternative embodiments, intramedullary rod plate 250 can include fewer or more than four holes 251 that can accommodate plate screws 160 or other fasteners. In some embodiments, intramedullary rod plate 250 includes plate hole 254 that allows for passage of threaded portion 226 of interlocking screw 225 through plate hole 254. The medial surface of head portion 227 may be configured to engage with the lateral surface of plate hole 254, thus achieving an interference frictional fit of interlocking screw head 227 with intramedullary plate 250. In alternative embodiments, the medial surface of head portion 227 may be configured with threads that engage and mate with a threaded lateral surface of plate hole 254, thus creating a locked threaded engagement.

In alternative embodiments, plate hole 254 may be eccentrically located in an intramedullary rod plate, rather than centrally located. In alternative embodiments, there may be more than one eccentrically-located plate hole 254, in which system there would be two or more sites of attachment of an intramedullary rod plate to an intramedullary rod via two or more interlocking screws.

Now, turning to FIG. 12B, a perspective view depicting interlocking screw 225 now inserted through intramedullary rod plate 250 (through hole 254 from FIG. 12A) and through hole 401 in intramedullary rod 400 is shown, in accordance with an illustrative embodiment. Plate screws 160 are shown in an assembling position. Hole 401 may include threads that mate with the threaded portion 226 of interlocking screw 225, or hole 401 may be thread-less, in which case in some embodiments the relationship between hole 401 and threaded shaft portion 226 would be configured to create an interference frictional fit between the threads of interlocking screw shaft 226 and the surface of hole 401. Head portion 227 of interlocking screw 225 engages intramedullary rod plate 250 by virtue of the medial-facing surface of head portion 227 (from FIG. 12A) pressing tightly against the lateral-facing surface of plate hole 254 (from FIG. 12A). As the medial-facing surface of head portion 227 presses tightly against the lateral-facing surface of plate hole 254, the medial surface of intramedullary rod plate 250 is pressed against the outer surface of distal femur 300 (from FIGS. 1A and 8A.). As interlocking screw 225 is advanced into femoral bone and achieves a frictional fit with bone, intramedullary rod plate 250 is further pressed against the outer surface of distal femur 300 (from FIGS. 1A and 8A), thus creating a frictional force between both the screw head 227 and plate 250 as well as a frictional force between both the plate 205 and the outer surface of the distal femur, until the perceived level of screw purchase and frictional force are achieved. This interaction of frictional forces amongst interlocking screw 225, intramedullary rod plate 250, intramedullary rod 400 and femoral bone would create a relatively rigid connection between intramedullary rod plate 250 and intramedullary rod 400, thus allowing for bone fixation using screws 160, as depicted in FIG. 12C.

Though it is not shown here, intramedullary rod fixation proximal to the fracture occurs via the mechanism described in FIG. 8A. With reference to FIG. 8A, intramedullary rod fixation proximal to the fracture occurs via the frictional fit of the outer surface of intramedullary rod 400 to the surface of the medullary canal of femur 105, and this proximal fixation may be augmented by placing interlocking screws 165 or fasteners through bone located towards the proximal end of the femur and through holes in the intramedullary rod 400 at the end of the intramedullary rod opposite the end of the rod with interlocking screw 225 (e.g., proximal interlocking screws).

Now, turning to FIG. 12C, a perspective view depicting interlocking screw 225 inserted through intramedullary rod plate 250 (through hole 254 from FIG. 12A) and through hole 401 (from FIG. 12A) in intramedullary rod 400, with plate screws 160 now inserted through intramedullary rod plate 250 is shown, in accordance with an illustrative embodiment. Head portion 227 of interlocking screw 225 engages intramedullary rod plate 250 by virtue of the medial-facing surface of head portion 227 pressing tightly against the lateral-facing surface of plate hole 254 (from FIG. 12A). As the medial-facing surface of head portion 227 presses tightly against the lateral-facing surface of plate hole 254 (from FIG. 12A), the medial surface of intramedullary rod plate 250 is pressed against the outer surface of distal femur 300 (from FIGS. 1A and 8A). As interlocking screw 225 is advanced into femoral bone and achieves a frictional fit with bone, intramedullary rod plate 250 is further pressed against the outer surface of distal femur 300 (from FIGS. 1A and 8A) thus creating a frictional force between both the interlocking screw head 227 and plate 250, as well as a frictional force between both the plate 205 and the outer surface of the distal femur, until the perceived level of screw purchase and frictional force are achieved. This interaction of fictional forces amongst interlocking screw 225, intramedullary rod plate 250, intramedullary rod 400, and femoral bone creates a relatively rigid connection between intramedullary rod plate 250 and intramedullary rod 400, thus allowing for bone fixation using screws 160. Screws 160 are inserted through plate holes 251 (from FIG. 12A) and threaded screw shafts 162 achieve a frictional fit with bone. As the screws 160 are inserted fully and screw heads 162 press tightly into plate holes 251 (from FIG. 12A) to achieve a frictional fit with intramedullary rod plate 250, fixation of the intramedullary rod plate system bone distal to the femur fracture 106 (from FIGS. 1A and 8A) is achieved.

Figure 13A:
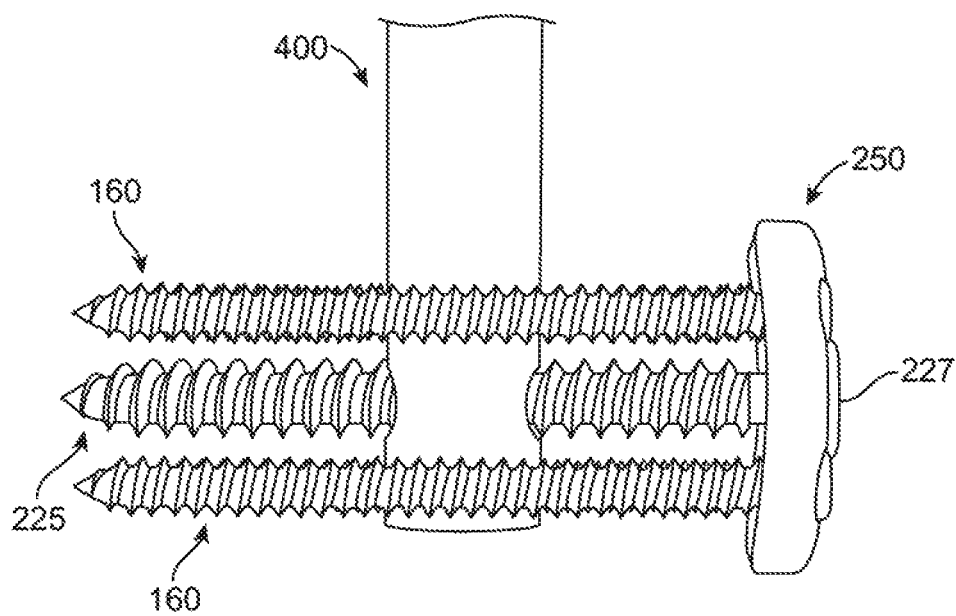
FIG. 13A is a top view depicting an assembled interlocking screw passed through the intramedullary rod plate and the intramedullary rod, with plate screws passed through the intramedullary rod plate, in accordance with an illustrative embodiment.

Turning now to FIG. 13A, a top view depicting an embodiment of the assembled intramedullary rod plate system is shown in accordance with an illustrative embodiment. Intramedullary rod plate 250 is secured to interlocking screw 225 via either a frictional fit or threaded engagement with interlocking screw head 227, and interlocking screw 225 has been inserted through intramedullary rod 400. Plate screws 160 are placed through holes 251 (from FIG. 12A) in intramedullary rod plate 250. Only two plate screws 160 are visible in this view because the two screws in the forefront overlap the two screws in the background. In an alternative embodiment, more or fewer screws 160 may be inserted through holes in an intramedullary rod plate.

Figure 13B:
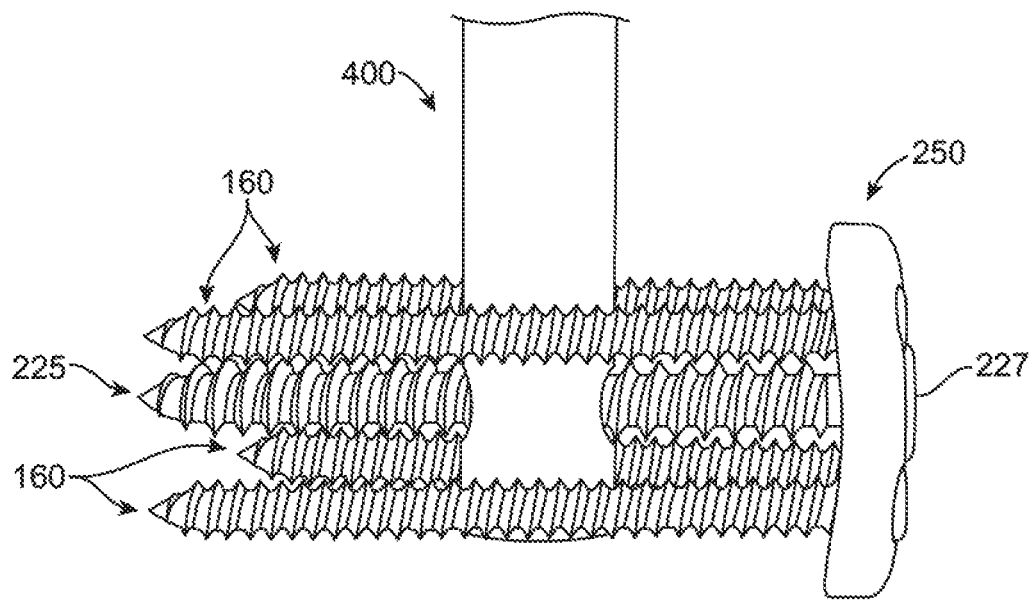
FIG. 13B is a top perspective view depicting an assembled interlocking screw passed through the intramedullary rod plate and the intramedullary rod, with plate screws passed through the intramedullary rod plate, in accordance with an illustrative embodiment.

Turning now to FIG. 13B, a top perspective view depicting the assembled intramedullary rod plate system is shown in accordance with an illustrative embodiment. Intramedullary rod plate 250 is secured to interlocking screw 225 via either a frictional fit or threaded engagement with interlocking screw head 227. The interlocking screw 225 has been inserted through intramedullary rod 400, with plate screws 160 placed through holes 251 (from FIG. 12A) in intramedullary rod plate 250.

Figure 14A:
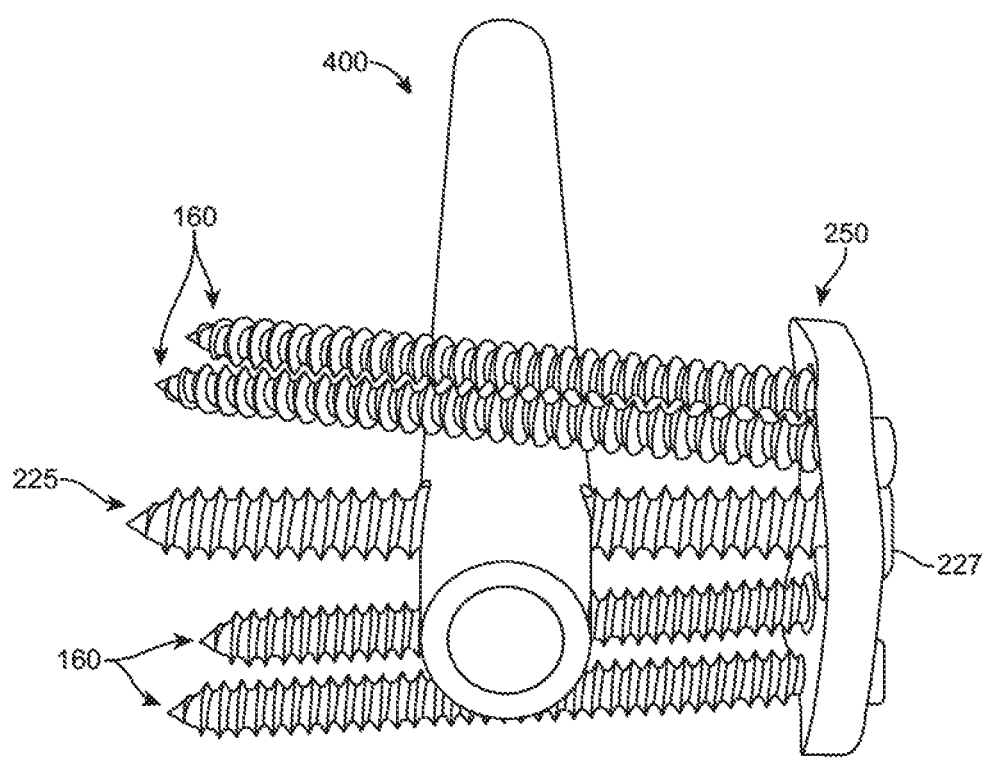
FIG. 14A is an end perspective view depicting an assembled interlocking screw passed through the intramedullary rod plate and the intramedullary rod, with plate screws passed through the intramedullary rod plate, in accordance with an illustrative embodiment.

Now turning to FIG. 14A, a perspective view depicting the assembled intramedullary rod plate system is shown in accordance with an illustrative embodiment. Intramedullary rod plate 250 is secured to interlocking screw 225 via either a frictional fit or threaded engagement with interlocking screw head 227. The interlocking screw 225 has been inserted through intramedullary rod 400, with plate screws 160 placed through holes 251 (from FIG. 12A) in intramedullary rod plate 250.

Figure 14B:
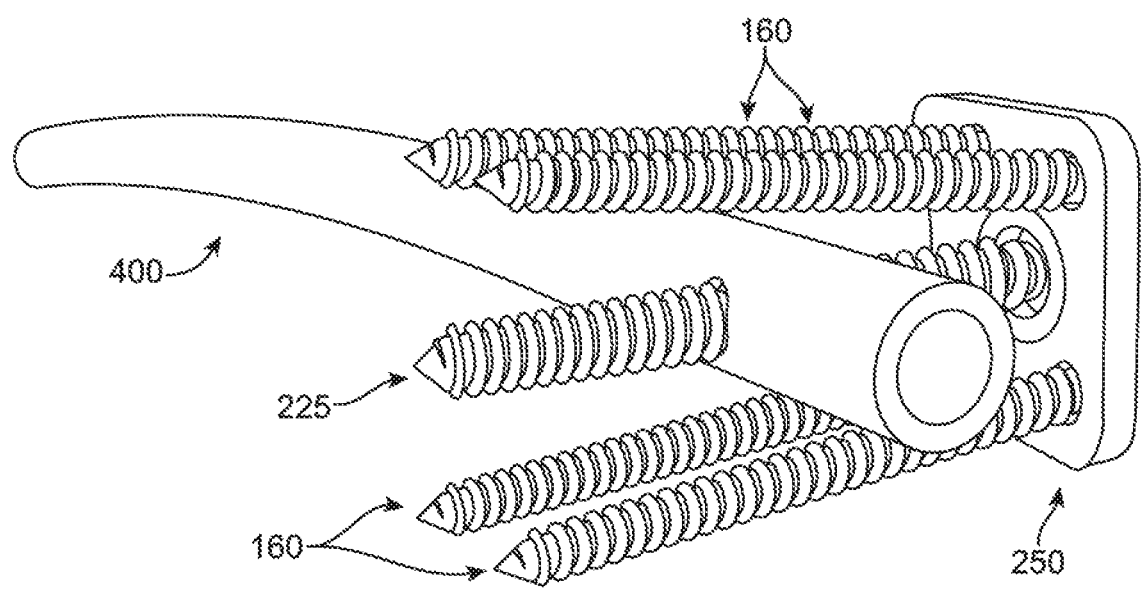
FIG. 14B is a perspective view depicting an assembled interlocking screw passed through the intramedullary rod plate and the intramedullary rod, with plate screws passed through the intramedullary rod plate, in accordance with an illustrative embodiment.

FIG. 14B is a perspective view depicting the assembled intramedullary rod plate system in accordance with an illustrative embodiment. Intramedullary rod plate 250 is secured to interlocking screw 225 via either a frictional fit or threaded engagement with interlocking screw head 227. The interlocking screw 225 has been inserted through intramedullary rod 400, with plate screws 160 placed through holes 251 (from FIG. 12A) in intramedullary rod plate 250.

Figure 15:
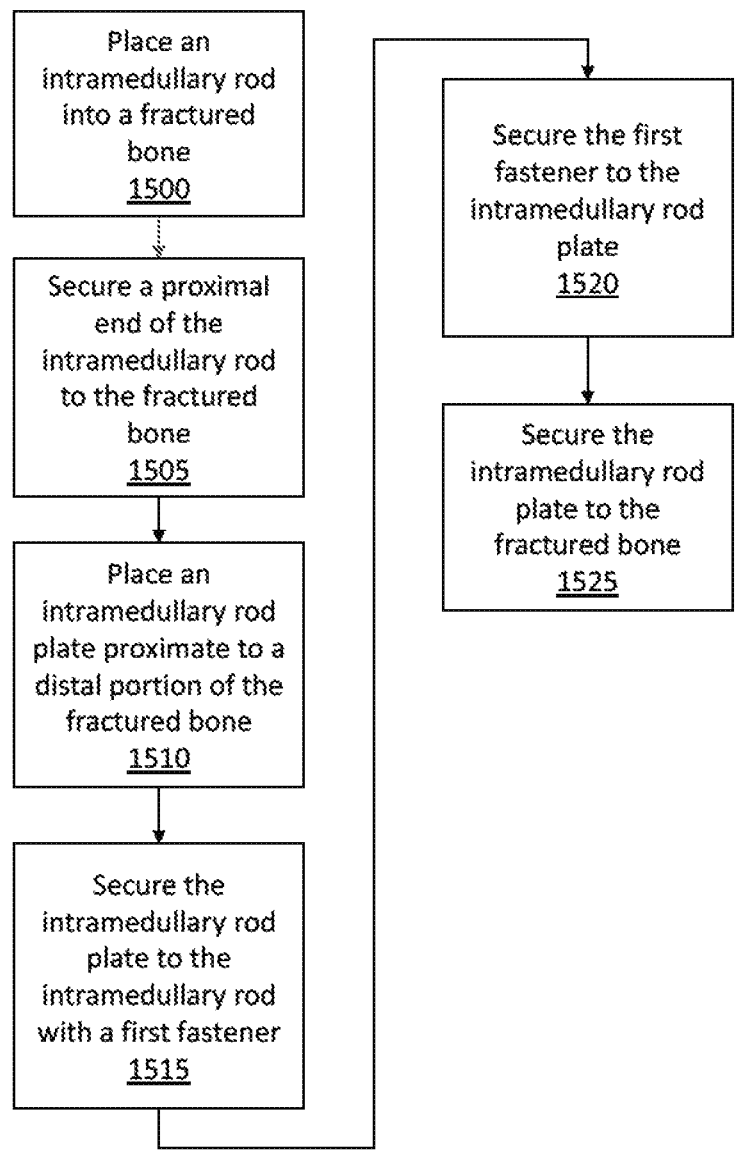
FIG. 15 is a flow diagram depicting operations performed to use an intramedullary rod plate system in accordance with an illustrative embodiment.

FIG. 15 is a flow diagram depicting operations performed to use an intramedullary rod plate system in accordance with an illustrative embodiment. In alternative embodiments, fewer, additional, and/or different operations may be performed. Also, the use of a flow diagram is not meant to be limiting with respect to the order of operations performed. In an operation 1500, an intramedullary rod is placed into a fractured bone. The intramedullary rod is placed into a medullary canal of the bone through an incision in the skin, and in accordance with techniques known to those of skill in the art. In an illustrative embodiment, the intramedullary rod spans a fracture in the bone such that a proximal end of the intramedullary rod is proximal to the fracture and a distal end of the intramedullary rod is distal to the fracture.

In an operation 1505, the proximal end of the intramedullary rod is secured to a proximal end of the bone. The proximal end can be secured by placing a screw or other fastener through the bone and into a hole in the proximal end of the intramedullary rod. Imaging may be used to place the screw or other fastener. In an operation 1510, an intramedullary rod plate is placed proximate to the distal portion of the fractured bone through an incision in the skin. Placement of the intramedullary rod plate may be assisted with the use of imaging.

In an operation 1515, the intramedullary rod plate is secured to the intramedullary rod with a first fastener. In one embodiment, the first fastener can be a blade. Alternatively, a bolt, screw, or other type of fastener may be used. In an illustrative embodiment, the first fastener includes a cylindrical head that is received by a cylindrical protrusion on a rear face of the intramedullary rod plate. In an operation 1520, the first fastener is secured to the intramedullary rod plate. In one implementation, an opening in the intramedullary rod plate that receives the first fastener is chamfered such that a head of a first fastener securing screw mates with the chamfered opening. The first fastener securing screw is threaded into the cylindrical head of the first fastener such that the first fastener is secured to the intramedullary rod plate. In an operation 1525, the intramedullary rod plate is secured to the fractured bone with one or more additional fasteners that travel through openings into the intramedullary rod plate and into the bone. Screws or any other type of fastener(s) may be used in operation 1525.

The embodiments described herein are not limited to use of a single intramedullary rod plate. For example, in one embodiment, the intramedullary rod plate system utilizes two intramedullary rod plates with a single rod to immobilize a fracture. In such an embodiment, a first intramedullary rod plate is positioned and mounted distal to the fracture as described herein. A second intramedullary rod plate is positioned and mounted proximal to the fracture using the same process. In an alternative embodiment, a single intramedullary rod plate may be used, and may be positioned and mounted proximal to the fracture. The decision regarding whether to use a single intramedullary rod plate (either proximal or distal to the fracture) or two intramedullary rod plates (one proximal and one distal) can be made during surgery depending on the clinical circumstances. In another alternative embodiment, a single, larger plate can be used which spans the fracture and which is secured to the bone and intramedullary rod both proximal and distal to the fracture.

The components (e.g., the intramedullary rod plate, intramedullary rod, interlocking fasteners, plate screws, and plate fasteners) described herein may be made in a variety of lengths and/or shapes to accommodate various patient anatomies and surgeon preferences. The components can be made from a variety of biologically compatible materials suitable for medical applications, including but not limited to metals, bone material, ceramics, and synthetic composites. For example, the components of a intramedullary rod plate system may be fabricated from materials such as titanium, titanium alloys, cobalt-chrome alloys, stainless steel, stainless steel alloys, thermoplastics such as polyether ether ketone (PEEK) and other similar substances, carbon fiber, carbon fiber composites, ceramics and composites, aluminum, allograft bone, xenograft bone, any combination of the above substances, or any suitable material that is able to withstand the biomechanical stresses under which they are placed.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations.

However, the use of such phrases should not be construed to imply that the introduction of a claim recitation by the indefinite articles "a" or "an" limits any particular claim containing such introduced claim recitation containing only one such recitation, even when the same claim includes the introductory phrases "one or more" or "at least one" and indefinite articles such as "a" or "an" (e.g., "a" and/or "an" should typically be interpreted to mean "at least one" or "one or more") the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both tennis. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the disclosure be defined by the claims appended hereto and their equivalents.

What is claimed is:

1. A system to stabilize a fracture, the system comprising:
   an intramedullary rod having a first end and a second end and configured for placement within a medullary bone canal of a bone, wherein the intramedullary rod includes a first rod hole at the second end;
   an intramedullary rod plate having a first plate hole and a second plate hole, wherein the intramedullary rod plate includes a cylindrical receiving part on an inner surface thereof such that the cylindrical receiving part faces the bone and the intramedullary rod, and wherein the cylindrical receiving part is aligned with the first plate hole;
   a first fastener that includes a shaft portion and a threaded head portion, wherein the shaft portion of the first fastener passes through the first plate hole, through the cylindrical receiving part, through an outer surface of the bone, and through the first rod hole at the second end of the intramedullary rod such that the first fastener secures the intramedullary rod plate to the intramedullary rod, and wherein the threaded head portion of the first fastener mates with threads in the first plate hole; and
   a second fastener configured to pass through the second plate hole and into the bone such that the second fastener secures the intramedullary rod plate to the bone.

2. The system of claim 1, wherein the cylindrical receiving part is configured to receive at least a portion of the shaft portion of the first fastener.

3. The system of claim 1, further comprising a chamfer on an outer surface of the intramedullary rod plate, wherein the chamfer surrounds the first plate hole.

4. The system of claim 3, wherein the threaded head portion of the first fastener is configured to mate with the chamfer.

5. The system of claim 1, further comprising a contour on an inner surface of the intramedullary rod plate, wherein the contour is configured to mate with an outer surface of the bone.

6. The system of claim 1, wherein the first plate hole is located in a center of the intramedullary rod plate.

7. The system of claim 1, wherein the first plate hole is located eccentrically in the intramedullary rod plate.

8. The system of claim 1, further comprising a third plate hole configured to receive a third fastener, a fourth plate hole configured to receive a fourth fastener, and a fifth plate hole configured to receive a fifth fastener, wherein the third fastener, the fourth fastener, and the fifth fastener are configured to pass through the outer surface of the bone to secure the intramedullary rod plate to the bone.

9. The system of claim 8, wherein the second plate hole, the third plate hole, the fourth plate hole, and the fifth plate hole at least partially surround the first plate hole.

10. The system of claim 1, wherein the intramedullary rod includes a second rod hole at the first end, wherein the second rod hole is configured to receive a third fastener to secure the intramedullary rod to the bone.

11. A method of stabilizing a fracture, the method comprising:
    placing an intramedullary rod having a first end and a second end into a medullary bone canal of a bone, wherein the intramedullary rod includes a first rod hole at the second end;
    placing an intramedullary rod plate proximate to the second end of the intramedullary rod, wherein the intramedullary rod plate includes a first plate hole and a second plate hole;
    placing a first fastener such that a shaft portion of the first fastener passes through the first plate hole, through an outer surface of the bone, and through the first rod hole at the second end of the intramedullary rod to secure the intramedullary rod plate to the intramedullary rod and such that a threaded head portion of the first fastener mates with threads in the first plate hole, wherein at least a portion of the shaft portion is received by a cylindrical extension of an inner aspect of the first plate hole, and wherein the cylindrical extension is aligned with the first plate hole such that the cylindrical extension faces the bone and the intramedullary rod; and placing a second fastener through the second plate hole and into the bone to secure the intramedullary rod plate to the bone.

12. The method of claim 11, further comprising placing the first fastener such that the threaded head portion mates with a chamfer that surrounds the first plate hole.

13. The method of claim 11, further comprising placing a third fastener through a second rod hole at the first end of the intramedullary rod to secure the first end of the intramedullary rod to the bone.

14. The method of claim 11, wherein the shaft portion of the first fastener is threaded, and wherein placing the first fastener comprises mating threads of the shaft portion with threads in the first rod hole.

15. The method of claim 11, wherein placing the intramedullary rod plate comprises mating a contour on an inner surface of the intramedullary rod plate with an outer surface of the bone.

16. The method of claim 11, further comprising placing a third fastener through a third plate hole of the intramedullary rod plate, placing a fourth fastener through a fourth plate hole of the intramedullary rod plate, and placing a fifth fastener through a fifth plate hole of the intramedullary rod plate, wherein the third fastener, the fourth fastener, and the fifth fastener are configured to pass through the outer surface of the bone to secure the intramedullary rod plate to the bone.

17. The method of claim 16, wherein the second plate hole, the third plate hole, the fourth plate hole, and the fifth plate hole are positioned proximate to corners of the intramedullary rod plate.

18. The method of claim 11, wherein the first plate hole is located in a center of the intramedullary rod plate.

* * * * *